US009907853B2

United States Patent
Maines

(10) Patent No.: US 9,907,853 B2
(45) Date of Patent: Mar. 6, 2018

(54) APPROACH TO TREATMENT OF HYPERGLYCEMIA USING A NANOPARTICLE ENCAPSULATED PEPTIDE

(71) Applicant: University of Rochester, Rochester, NY (US)

(72) Inventor: Mahin D. Maines, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 15/599,532

(22) Filed: May 19, 2017

(65) Prior Publication Data

US 2017/0333564 A1 Nov. 23, 2017

Related U.S. Application Data

(60) Provisional application No. 62/339,314, filed on May 20, 2016.

(51) Int. Cl.
| | |
|---|---|
| *A61K 38/00* | (2006.01) |
| *A61K 47/42* | (2017.01) |
| *A61K 9/51* | (2006.01) |
| *A61K 38/16* | (2006.01) |
| *C07K 7/06* | (2006.01) |
| *C07K 7/08* | (2006.01) |

(52) U.S. Cl.
CPC ............ *A61K 47/42* (2013.01); *A61K 9/51* (2013.01); *A61K 38/16* (2013.01); *C07K 7/06* (2013.01); *C07K 7/08* (2013.01); *G01N 2800/042* (2013.01)

(58) Field of Classification Search
None
See application file for complete search history.

(56) References Cited

U.S. PATENT DOCUMENTS 9,567,601 B2 * 2/2017 Hymus ............ C12N 15/8269

OTHER PUBLICATIONS

Abraham and Kappas, "Pharmacological and clinical aspects of heme oxygenase," 2008, Pharmacol Rev 60:79-127.
Agarwal and Bolisetty, "Adaptive responses to tissue injury: role of heme oxygenase-1," 2013, Trans Am Clin Climatol Assoc 124:111-22.
Ahmad et al., "Human biliverdin reductase is a leucine zipper-like DNA-binding protein and functions in transcriptional activation of heme oxygenase-1 by oxidative stress," 2002, J Biol Chem 277:9226-32.
Ali et al., "Glycogen synthase kinase-3: properties, functions, and regulation," 2001, Chem Rev 101:2527-40.
Amrani et al., "Progression of autoimmune diabetes driven by avidity maturation of a T-cell population," 2000, Nature 406:732-42.
Barone et al., "Characterization of the S-denitrosylating activity of bilirubin," 2009, J Mol Methods 13(8):2365-75.
Biswas et al., "Nuclear heme oxygenase-1 (HO-1) modulates subcellular distribution and activation of Nrf2, impacting metabolic and anti-oxidant defenses," 2014, J Biol Chem 289:26882-94.
Brodbeck et al., "A human protein kinase B with regulatory phosphorylation sites in the activation loop and in the C-terminal hydrophobic domain," 1999, J Biol Chem 274:9133-6.
Buller et al., "A GSK-3/TSC2/mTOR pathway regulates glucose uptake and GLUT1 glucose transporter expression," 2008, Am J Physiol Cell Physiol 294:C836-43.
Cai et al., 2003, "Two new substrates in insulin signaling, IRS5/DOK4 and IRS6/DOK5," J Biol Chem 278:25323-30.
D'Archivio et al., "Predominant role of obesity/insulin resistance in oxidative stress development," 2012, Eur J Clin Invest 42:70-8.
Datta et al., "Cellular survival: a play in three akts," 1999, Genes Dev 13:2905-27.
Ding et al., "The coordinated increased expression of biliverdin reductase and heme oxygenase-2 promotes cardiomyocyte survival: a reductase-based peptide counters β-adrenergic receptor ligand-mediated cardiac dysfunction," 2011, FASEB J 25:301-13.
Dore et al., "Bilirubin, formed by activation of heme oxygenase-2, protects neurons against oxidative stress injury," 1999, PNAS 96(5):2445-50.
Favelyukis et al., "Structure and autoregulation of the insulin-like growth factor 1 receptor kinase," 2001, Nat Struct Biol 8:1058-63.
Frojdo et al., "Alterations of insulin signaling in type 2 diabetes: a review of the current evidence from humans," 2009, Biochimica et biophysica acta 1729:83-92.
Geraldes et al., "Selective regulation of heme oxygenase-1 expression and function by insulin through. IRS1/phosphoinositide 3-kinase/Akt-2 pathway," 2008, J Biol Chem 283:34327-36.
Gibbs et al., "Nanoparticle Delivered Human Biliverdin Reductase-Based Peptide Increases Glucose Uptake by Activating IRK/Akt/GSK3 Axis: The Peptide Is Effective in the Cell and Wild-Type and Diabetic Ob/Ob Mice" 2016, J Diabetes Res 4712053.
Gibbs et al., "Formation of ternary complex of human biliverdin reductase-protein kinase Cd-ERK2 protein is essential for ERK2-mediated activation of Elk1 protein, nuclear factor-?B, and inducible nitric-oxidase synthase (iNOS)," 2012, J Biol Chem 287:1066-79.
Gibbs et al., "Human biliverdin reductase-based peptides activate and inhibit glucose uptake through direct interaction with the kinase domain of insulin receptor," 2014, FASEB J 28:2478-91.
Goodman et al., "Heme oxygenase-2 deficiency contributes to diabetes-mediated increase in superoxide anion and renal dysfunction," 2006, J Am Soc Nephrol 17:1073-81.

(Continued)

*Primary Examiner* — Jeanette Lieb
(74) *Attorney, Agent, or Firm* — Riverside Law LLP

(57) ABSTRACT

The present invention relates to compositions and methods for treating or preventing hyperglycemia and diseases associated with hyperglycemia. In certain embodiments, the composition comprises a peptide having the amino acid sequence KRSCYK wherein the peptide consists of D-amino acids is useful in treating or preventing diabetes. In some aspects, the peptide of the invention is encapsulated in a nanoparticle.

14 Claims, 7 Drawing Sheets

(56) References Cited

OTHER PUBLICATIONS

Grieco et al., "Immunology in the clinic review series; focus on type 1 diabetes and viruses: how viral infections modulate beta cell function." 2012, Clin Exp Immunol 168:24-9.
Gunton et al., "Loss of ARNT/HIF1β mediates altered gene expression and pancreatic-islet dysfunction in human type 2 diabetes," 2005, Cell 122:337-49.
Hanada et al., "Structure, regulation and function of PKB/AKT—a major therapeutic target," 2004, Biochimica et biophysica acts 1697:3-16.
Hemmings and Restuccia, "Pl3K-PKB/Akt pathway," 2012, Cold Spring Harb Perspect Biol 4:a011189.
Hernandez et al., "Akt mediates insulin induction of glucose uptake and up-regulation of GLUT4 gene expression in brown adipocytes," 2001, FEBS Lett 494:225-31.
Holst et al., "Rapid analysis of T-cell selection in vivo using T cell-receptor retrogenic mice," 2006, Nat Methods 3:191-7.
Hu et al., "Systemic expression of heme oxygenase-1 ameliorates type 1 diabetes in NOD mice," 2007, Diabetes 56:1240-7.
Jones et al., "Molecular cloning and identification of a serine/threonine protein kinase of the second-messenger subfamily," 1991, PNAS 88:4171-5.
Khan and Chakrabarti, "Cellular signaling and potential new treatment targets in diabetic retinopathy," 2007, Exp Diabetes Res 2007:31867.
Khan et al., "Neuroprotective effect of hemeoxygenase-1/glycogen synthase kinase-3β modulators in 3-nitropropionic acid-induced neurotoxicity in rats," 2015, Neuroscience 287:66-77.
Khoo et al., "Regulation of insulin gene transcription by ERK1 and ERK2 in pancreatic β cells," 2003, J Biol Chem 278:32969-77.
Kikuchi et al., "Crystal structure of rat biliverdin reductase," 2001, Nat Struct biol 8:221-5.
Kim and Huang, "Nanoparticle delivery of a peptide targeting EGFR signaling," 2012, J Control Release 157:279-86.
Kravets et al., "Biliverdin reductase, a novel regulator for induction of activating transcription factor-2 and heme oxygenase-1," 2004, 1 Biol Chem 279:19916-23.
Lavan et al., "A novel 160-kDa phosphotyrosine protein in insulin-treated embryonic kidney cells is a new member of the insulin receptor substrate family," 1997, J Biol Chem 272:21403-7.
Lee and Pilch, "The insulin receptor: structure, function, and signaling," 1994, Am J Physiol 266:C319-34.
Lerner-Marmarosh et al., "Human biliverdin reductase: a member of the insulin receptor substrate family with serine/threonine/tyrosine kinase activity," 2005, PNAS 102:7109-14.
Lerner-Marmarosh et al., "Regulation of TNF-alpha-activated PKC-zeta signaling by the human biliverdin reductase: identification of activating and inhibitory domains of the reductase," 2007, FASEB J 21:3949-62.
Lerner-Marmarosh et al., "Human biliverdin reductase is an ERK activator; hBVR is an ERK nuclear transporter and is required for MAPK signaling," 2008, PNAS 105:6870-5.
Lesniak et al., "Nanoparticle adhesion to the cell membrane and its effect on nanoparticle uptake efficiency," 2013, J Am Chem Soc 134(4):1438-44.
Maines et al., "Characterization of two constitutive forms of rat liver microsomal heme oxygenase. Only one molecular species of the enzyme is inducible," 1986, J Biol Chem 261:411-9.
Maines et al., "Human biliverdin IXa reductase is a zinc-metalloprotein, Characterization of purified and *Escherichia coli* expressed enzymes," 1996, Eur J Biochem 235:372-81.
Maines et al., "Human biliverdin reductase, a previously unknown activator of protein kinase C βII," 2007, J Biol Chem 282:8110-22.
Maines, "Biliverdin reductase: PKC interaction at the cross-talk of MAPK and PI3K signaling pathways," 2007, Antioxid Redox Signal 9:2187-95.
McGregor, "Discovering and improving novel peptide therapeutics," 2008, Curr Opin Pharmacol 8:616-9.
Miralem et al., "Small interference RNA-mediated gene silencing of human biliverdin reductase, but not that of heme oxygenase-1, attenuates arsenite-mediated induction of the oxygenase and increases apoptosis in 293A kidney cells," 2005, J Biol chem 280:17084-92.
Miralem et al., "The human biliverdin reductase-based peptide fragments and biliverdin regulate protein kinase Cd activity: the peptides are inhibitors or substrate for the protein kinase C," 2012, J Biol Chem 287:24698-712.
Mancuso et al., "Bilirubin and S-nitrosothiols interaction: evidence for a possible role of bilirubin as a scavenger of nitric oxide," 2003, Biochem Pharmaol 66(12):1355-63.
Mancuso et al., "Inhibition of heme oxygenase in the central nervous system potentiates endotoxin-induced vasopressin release in the rat," 1999, J Nueroimmunol (2) 189-94.
Mancuso et al., "Activation of heme oxygenase and consequent carbon monoxide formation inhibits the release of arginine vasopressin from rat hypothalamic explants. Molecular linkage between heme catabolism and neuroendocrine function," 1997, Mol Brain Res 50(1-2):267-76.
Naidu et al., "An atypical NF-kB-regulated pathway mediates phorbol ester-dependent heme oxygenase-1 gene activation in monocytes," 2008, J Immunol 181:4113-23.
Nakao et al., "Protection against ischemia/reperfusion injury in cardiac and renal transplantation with carbon monoxide, biliverdin and both," 2005, Am J Transplant 5:282-91.
Orena et al., "Inhibition of glycogen-synthase kinase 3 stimulates glycogen synthase and glucase transport by distinct mechanisms in 3T3-L1 adipocytes," 2000, J Biol Chem 275:15765-72.
Paine et al., "Signaling to heme oxygenase-1 and its anti-inflammatory therapeutic potential," 2010, Biochem Pharmacol 80:1895-903.
Pozzoli et al., "Carbon monoxide as a novel neuroendocrine modulator: inhibition of stimulated corticotropin-releasing hormone release from acute rat hypothalamic explants," 1994, Endocrinol 234(1-2):372-81.
Provost et al., "Viral 2A peptides allow expression of multiple proteins from a single ORF in transgenic zebrafish embryos," 2007, Genesis 45:625-9.
Rayasam et al., "Glycogen synthase kinase 3: more than a namesake," 2009, Br J Pharmacol 156:885-98.
Riley et al., "Phosphatidylinositol 3-kinase activity is critical for glucose metabolism and embryo survival in murine blastocysts," 2006, J Biol Chem 281:6010-9.
Rocchi et al., "Determination of Gab1 (Grb2-associated binder-1) interaction with insulin receptor-signaling molecules," 1998, Mol Endocrinol 12:914-23.
Ryter et al., "HeMe oxygenase-1/carbon monoxide: from basic science to therapeutic applications," 2006, Physiol Rev 86:583-650.
Saha et al., "Acute hyperglycemia induced by ketamine/xylazine anesthesia in rats: mechanisms and implications for preclinical models," 2005, exp Biol Med 230:777-84.
Salazar et al., "Glycogen synthase kinase-3β inhibits the xenobiotic and antioxidant cell response by direct phosphorylation and nuclear exclusion of the transcription factor Nrf2," 2006, J Biol Chem 281:14841-51.
Salim et al., "Human biliverdin reductase is autophosphorylated, and phosphorylation is required for bilirubin formation," 2001, J Biol Chem 276:10929-34.
Sato et al., "Therapeutic peptides: technological advances driving peptides into development," 2006, Curr Opin Biotechnol 17:638-42.
Shinohara et al., "Silencing glycogen synthase kinase-3β inhibits acetaminophen hepatotoxicity and attenuates JNK activation and loss of glutamate cysteine ligase and myeloid cell leukemia sequence 1," 2010, J Biol Chem 285:8244-55.
Shoelson et al., "YMXM motifs of IRS-1 define substrate specificity of the insulin receptor kinase," 1992, PNAS 89:2027-31.
Soares and Bach, "Heme oxygenase-1: from biology to therapeutic potential," 2009, Trends Mol Med 15:50-8.
Stephens et al., "Protein kinase B kinases that mediate phosphatidylinositol 3,4,5-trisphosphate-dependent activation of protein kinase B," 1998, Science 279:710-4.
Stocker et al., "Bilirubin is an antioxidant of possible physiological importance," 1987, Science 235:1043-6.

(56) References Cited

OTHER PUBLICATIONS

Stocker et al., "Antioxidant activities of bile pigments," 2004, Antioxid Redox Signal 6:841-9.
Stokoe et al., "Dual role of phosphatidylinositol-3,4,5-trisphosphate in the activation of protein kinase B," 1997, Science 277:567-70.
Tschopp et al., "Essential role of protein kinase B (PKB/Akt3) in postnatal brain development but not in glucose homeostasis," 2005, Development 132:2943-54.
Tudor et al., "Biliverdin reductase is a transporter of haem into the nucleus and is essential for regulation of HO-1 gene expression by haematin," 2008, Biochem J 413:405-16.
Vitek, 2012, "The role of bilirubin in diabetes, metabolic syndrome, and cardiovascular diseases," Front Pharmacol 3:55.
Ward et al., "The insulin receptor changes conformation in unforeseen ways on ligand binding: sharpening the picture of insulin receptor activation." 2013, Bioessays 35:945-54.
Wegiel et al., "Cell surface biliverdin reductase mediates biliverdin-induced anti-inflammatory effects via phosphatidylinositol 3-kinase and Akt," 2009, J Biol Chem 284:21369-78.
Whitby et al., "Crystal structure of a biliverdin IXa reductase enzyme-cofactor complex," 2002, J Mol Biol 319:1199-210.
Williams et al., "Hemoxygenase-2 is an oxygen sensor for a calcium-sensitive potassium channel," 2004, Science 306:2093-7.

\* cited by examiner

```
                         SEQUENCE LISTING

<160> NUMBER OF SEQ ID NOS: 9

<210> SEQ ID NO 1
<211> LENGTH: 7
<212> TYPE: PRT
<213> ORGANISM: Artificial Sequence
<220> FEATURE:
<223> OTHER INFORMATION: chemically synthesized

<400> SEQUENCE: 1

Lys Arg Ser Cys Cys Tyr Lys
1               5

<210> SEQ ID NO 2
<211> LENGTH: 7
<212> TYPE: PRT
<213> ORGANISM: Artificial Sequence
<220> FEATURE:
<223> OTHER INFORMATION: chemically synthesized

<400> SEQUENCE: 2

Lys Tyr Cys Cys Ser Arg Lys
1               5

<210> SEQ ID NO 3
<211> LENGTH: 7
<212> TYPE: PRT
<213> ORGANISM: Artificial Sequence
<220> FEATURE:
<223> OTHER INFORMATION: chemically synthesized

<400> SEQUENCE: 3

Tyr Lys Cys Lys Cys Arg Ser
1               5

<210> SEQ ID NO 4
<211> LENGTH: 7
<212> TYPE: PRT
<213> ORGANISM: Artificial Sequence
<220> FEATURE:
<223> OTHER INFORMATION: chemically synthesized

<400> SEQUENCE: 4

Ser Arg Cys Lys Cys Lys Tyr
1               5

<210> SEQ ID NO 5
<211> LENGTH: 7
<212> TYPE: PRT
<213> ORGANISM: Artificial Sequence
<220> FEATURE:
```

```
<223> OTHER INFORMATION: chemically synthesized

<400> SEQUENCE: 5

Lys Lys Arg Ile Leu His Cys
1               5

<210> SEQ ID NO 6
<211> LENGTH: 8
<212> TYPE: PRT
<213> ORGANISM: Artificial Sequence
<220> FEATURE:
<223> OTHER INFORMATION: chemically synthesized

<400> SEQUENCE: 6

Lys Arg Asn Arg Tyr Leu Ser Phe
1               5

<210> SEQ ID NO 7
<211> LENGTH: 13
<212> TYPE: PRT
<213> ORGANISM: Artificial Sequence
<220> FEATURE:
<223> OTHER INFORMATION: chemically synthesized

<400> SEQUENCE: 7

Gly Arg Pro Arg Thr Ser Ser Phe Ala Glu Gly Lys Lys
1               5                   10

<210> SEQ ID NO 8
<211> LENGTH: 8
<212> TYPE: PRT
<213> ORGANISM: Artificial Sequence
<220> FEATURE:
<223> OTHER INFORMATION: chemically synthesized

<400> SEQUENCE: 8

Lys Lys Glu Val Val Gly Lys Asp
1               5

<210> SEQ ID NO 9
<211> LENGTH: 7
<212> TYPE: PRT
<213> ORGANISM: Artificial Sequence
<220> FEATURE:
<223> OTHER INFORMATION: chemically synthesized

<400> SEQUENCE: 9

Lys Phe Cys Cys Ser Arg Lys
1               5
```

US 9,907,853 B2

APPROACH TO TREATMENT OF HYPERGLYCEMIA USING A NANOPARTICLE ENCAPSULATED PEPTIDE

CROSS-REFERENCE TO RELATED APPLICATIONS

The present application is entitled to priority to U.S. Provisional Application No. 62/339,314, filed May 20, 2016, which is incorporated by reference herein in its entirety.

STATEMENT REGARDING FEDERALLY SPONSORED RESEARCH OR DEVELOPMENT

This invention was made with government support under NIHES-RO1-004066 awarded by National Institutes of Health. The government has certain rights in the invention.

BACKGROUND OF THE INVENTION

The defect leading to type-1 diabetes is autoimmune ablation of the pancreatic β-cells, including those arising from infection, causing severely impaired glucose uptake from the circulation (Amrani et al., 2000, Nature 406:732-42; Galleri et al., 2012, Adv Exp Med Biol 771:252-71; Grieco et al., 2012, Clin Exp Immunol 168:24-9). In type-2 diabetes, the insulin signaling cascade is impaired in the insulin responsive tissues: skeletal muscle, adipose tissue and liver (Frojdo et al., 2009, Biochimica et biophysica acta 1729:83-92). The action of insulin as a metabolic regulator and a growth factor is protein tyrosine kinase (PTK)-dependent and is an essential step in the initiation of signaling cascade initiated by its cell surface receptor. The insulin receptor is a heterotetramer of two α- and two β-subunits (Lee and Pilch, 1994, Am J Physiol 266:C319-34; Ward et al., 2013, Bioessays 35:945-54). The α-subunits are entirely extracellular and contain the ligand-binding site. The β-subunits are composed of three domains: extracellular, which is disulfide bonded to the C-terminal region of the α-subunits, transmembrane and cytosolic. The cytosolic domain in include a tyrosine kinase domain (IRK) contains three tyrosine residues, $Y^{1158,1162,1163}$ that are autophosphorylated upon ligand binding to the α subunits. Autophosphorylation stimulates a change in conformation of the activation loop that is necessary for binding and tyrosine phosphorylation of proteins containing YMXM sequence (Shoelson et al., 1992, PNAS 89:2027-31) including IRS1, IRS2, PI3K and BVR, and allows assembly of multi-protein signaling complexes (Lavan et al., 1997, J Biol Chem 272:21403-7; Rocchi et al., 1998, Mol Endocrinol 12:914-23; White and Yunesh, 1998, Curr Top Microbiol Immunol 228:179-208; Cai et al., 2003, J Biol Chem 278:25323-30; Grusovin and Macaulay, 2003, Front Biosci 8:d620-41; Lerner-Marmarosh et al., 2005, PNAS 102:7109-14). Defective insulin signal transduction is associated with molecular defects in the signaling pathway, the evaluation of which has largely focused on major nodes in the pathways—the insulin receptor itself, insulin receptor substrates 1 and 2, PI3K, Akt/PKB, atypical PKCs (aPKCs, i.e. ζ or λ) and MAPKs (Frojdo et al., 2009, Biochimica et biophysica acta 1729: 83-92).

Activation of IRK stimulates the Akt/GSK axis, which is vital for glucose uptake and metabolism (Hernandex et al., 2001, FEBS Lett 494:225-31; Riley et al., 2006, J Biol Chem 281:6010-9). Activated IRK phosphorylates the adapter molecules IRS1 and IRS2, which in turn recruit other proteins to the complex including PI3K. Activation of PI3K results in synthesis of phosphatidylinositol-3-phosphates, which act as membrane anchors for pleckstrin homology domain-containing proteins, such as PKCs, PDK1 and Akts (1-3). Three Akt isoforms have been characterized (Jones et al., 1991, PNAS 88:4171-5; Datta et al., 1999, Genes Dev 13:2905-27); Akt1 is the most intensely studied isoform. Unlike Akt1 or Akt2, Akt3, which is highly expressed in testis and brain, appears to play no role in glucose homeostasis (Brodbeck et al., 1999, J Biol Chem 274:9133-6; Tschopp et al., 2005, Development 132:2943-54). The catalytic domain of all Akt kinases has a threonine residue in the activation loop, $T^{308}$, that is phosphorylated by PDK1 after both proteins have been recruited to the membrane. A second phosphorylation, at $S^{473}$ in the hydrophobic loop leads to maximal activity (Stokoe et al., 1997, Science 277:567-70; Stephens et al., 1998, Science 279:710-4). The mechanism of serine phosphorylation has been attributed to autophosphorylation and to several other kinases (Hanada et al., 2004, Biochimica et biophysica acta 1697:3-16; Hemmings and Restuccia, 2012, Cold Spring Harb Perspect Biol 4:a011189). A threonine$^{450}$ in the turn motif of the C-terminal regulatory domain is also a phosphorylation target; modification of this residue, however, is not required for full activity. Activated Akt in turn regulates a wide variety of cellular functions, including that of one of its substrates, glucose synthase kinase-3 (GSK3). The GSK-3 α and β isoforms are inactivated after phosphorylation by Akt; inactivation of GSK3 stimulates glucose uptake and also allows activation of glycogen synthase, and hence synthesis of glycogen (Orena et al., 2000, J Biol Chem 275:15765-72; Buller et al., 2008, Am J Physiol Cell Physiol 294:C836-43).

Human (h)BVR is a 296 residue soluble protein that was initially described as being the sole cellular source of bilirubin, a most potent intracellular quencher of free radicals (Stocker et al., 1987, Science 235:1043-6; Stocker et al., 2004, Antioxid Redox Signal 6:841-9; Vitek, 2012, Front Pharmacol 3:55). However, hBVR is also a bZip (basic zipper) transcription factor for regulation of stress response genes, including ATF2/CREB (Kravets et al., 2004, J Biol Chem 279:19916-23; Ahmad et al., 2002, J Biol Chem 277:9226-32) and a Ser/Thr/Tyr kinase that is activated by IRK (Lerner-Marmarosh et al., 2005, PNAS 102:7109-14; Salim et al., 2001, J Biol Chem 276:10929-34) hBVR translocates, depending on the stimulus, to and from the nucleus, cytoplasm or cell membrane (Lerner-Marmarosh et al., 2007, FASEB J 21:3949-62; Lerner-Marmarosh et al., 2008, PNAS 105:6870-5; Maines et al., 2007, J Biol Chem 282:8110-22; Tudor et al., 2008, Biochem J 413:405-16) and in so doing functions as a scaffold and as an intracellular carrier protein (Kravets et al., 2004, J Biol Chem 279:19916-23; Ahmad et al., 2002, J Biol Chem 277:9226-32; Lerner-Marmarosh et al., 2008, PNAS 105:6870-5; Maines et al., 2007, J Biol Chem 282:8110-22; Gibbs et al., 2012, J Biol Chem 287:1066-79; Miralem et al., 2005, J Biol chem 280:17084-92). The structural features of the protein are of relevance to its many functions (Maines et al., 1996, Eur J Biochem 235:372-81; Whitby et al., 2002, J Mol Biol 319:1199-210; Kikuchi et al., 2001, Nat Struct biol 8:221-5); the N-terminal domain includes the active site and residues involved in ATP/NADPH binding, whereas the C-terminal domain includes a large six-stranded β-sheet followed by an α-helix that forms an ideal surface for protein: protein interaction.

Insulin was shown to regulate components of heme degradation pathway. It induced HO-1 expression through IRS1/PI3K/Akt2 pathway (Geraldes et al., 2008, J Biol Chem 283:34327-36). Also, hBVR was shown to be a substrate for the insulin receptor kinase (Lerner-Marmarosh et al., 2005, PNAS 102:7109-14), which phosphorylates three tyrosine residues in the protein: protein interactive domain in vitro. One of these, $Y^{198}$, is in a canonical IRK substrate motif, YMKM, while $Y^{228}$ in the YLSF motif that meets YΦSΦ criteria for an IRK target (Favelyukis et al., 2001, Nat Struct Biol 8:1058-63) and $Y^{291}$ is in the C-terminal helix of hBVR (aa271-296) (Lerner-Marmarosh et al., 2005, PNAS 102:7109-14). hBVR functions have been systematically dissected using synthetic peptides based on its primary sequence, and tested the peptides in vitro and in cell culture systems; one such fragment corresponding to its C-terminal 7 residues, $K^{291}$YCCRSK (hereinafter P2) is an activator of IRK, by means of a novel intracellular interaction with the kinase and stimulator of glucose uptake (Gibbs et al., 2014, FASEB J 28:2478-91). The peptide was shown to increase IRK Vmax, without changing Km of the kinase. It stimulated glucose uptake in 4 cell lines tested so far. Change in fluorescence emission spectra of IRK domain (aa 988-1263), with fluorophore coupled to cysteines, $C^{1056}$, $C^{1138}$ or $C^{1234}$ in the presence of KYCCSRK (SEQ ID NO: 2) indicated that the peptide bound to and changed IRK conformation. Binding of the sequence to IRK was substantiated by finding that KYCCSRK (SEQ ID NO: 2) sequence in intact hBVR was necessary for the hBVR/IRK cross-activation (Gibbs et al., 2014, FASEB J 28:2478-91).

P2 stimulates glucose uptake in several cell types, including cells derived from liver (HepG2), kidney (HEK), pulmonary artery smooth muscle (PASM) and skeletal muscle myoblasts, using an N-myristoylated form of the peptide synthesized using the naturally occurring L-enantiomeric amino acids. This form was membrane permeable and effective for a brief period in the cultured cells (Gibbs et al., 2014, FASEB J 28:2478-91). For a number of reasons, this composition is unsuitable for use as a therapeutic agent; small molecules (MW <5 kDa) are rapidly depleted in the circulation and excreted via the kidneys, and moreover the L-amino acid peptides are highly susceptible to proteolytic degradation (Sato et al., 2006, Curr Opin Biotechnol 17:638-42; McGregor, 2008, Curr Opin Pharmacol 8:616-9).

Thus, there is a need in the art for compositions and methods for treating diabetes. The present invention satisfies this unmet need.

SUMMARY OF THE INVENTION

In one aspect, the invention provides an isolated peptide comprising an amino acid sequence of KRSCCYK (SEQ ID NO: 1). In one embodiment, each amino acid of the isolated peptide is in D-configuration (D-amino acid). In one embodiment, the peptide comprises an acetyl group. In one embodiment, the acetyl group is on the N-terminus of the peptide. In one embodiment, the peptide comprises an amido group. In one embodiment, the amido group is on the C-terminus of the peptide.

In another aspect, the present invention provides a composition comprising an isolated peptide comprising an amino acid sequence of KRSCCYK (SEQ ID NO: 1), wherein each amino acid of the peptide is in D configuration (D-amino acid). In one embodiment, the composition comprises a pharmaceutically acceptable carrier.

In one embodiment, the composition is in the form of a nanoparticle. In one embodiment, the nanoparticle comprises a core comprising heparin, protamine, and the peptide. In one embodiment, the weight ratio of protamine to heparin is about 0.3:1 to about 0.6:1. In one embodiment, the nanoparticle comprises a membrane comprising cholesterol and DOTAP.

In another aspect, the present invention provides a method for treating diabetes in a subject. In one embodiment, the method comprises administering to a subject an effective amount of an isolated peptide comprising an amino acid sequence of KRSCCYK (SEQ ID NO: 1), or a composition comprising an isolated peptide comprising an amino acid sequence of KRSCCYK (SEQ ID NO: 1). In one embodiment, peptide comprises an acetyl group on the N-terminus of the peptide. In one embodiment, wherein the peptide comprises an amido group on the C-terminus of the peptide. In one embodiment, the method further comprises administering a second therapeutic agent. In one embodiment, the second therapeutic agent is an anti-diabetic agent. In one embodiment, the second therapeutic agent is insulin.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A through FIG. 1D depicts results of experiments demonstrating the construction of nanoparticles.

FIG. 2, comprising FIG. 2A through FIG. 2C depicts results of experiments demonstrating P2 nanoparticles induce glucose uptake in cells.

FIG. 3, comprising FIG. 3A through FIG. 3D depicts results of experiments demonstrating P2 nanoparticles modulate circulating glucose level.

FIG. 4, comprising FIG. 4A depicts P2 stimulate IRK autophosphorylation in vitro. IRK was incubated in vitro with 20 µM of peptide P2 (KYCCSRK (SEQ ID NO: 2)), peptide a (KKRILHC (SEQ ID NO: 5)) or peptide b (KRNRYLSF (SEQ ID NO: 6)) and [$^{32}$P]-ATP. The [$^{32}$P] incorporation was quantified. FIG. 4B depicts P2 stimulate IRK kinase activity in vitro; identification of IRK inhibitory peptide. A similar assay was performed as in FIG. 4A, except that the IRK peptide substrate was included. FIG. 4C depicts P2 is both a substrate and activator of IRK kinase activity in vitro. Assays using sequence variant (P2Y-F; KFCCSRK (SEQ ID NO: 9)) of P2 were performed as in FIG. 4B. FIG. 4D depicts P2 stimulates IRK kinase activity in the cell; peptide "a" is an inhibitor. HEK cells were serum-starved overnight and treated with the indicated myristoylated peptides (40 µM) for 15 minutes IRK was immunoprecipitated from cell lysates and assayed using the IRS peptide as substrate. FIG. 4E depicts Activation of liver IRK by nanoparticle P2. C57B1/6J mice were deprived of food overnight, anesthetized with ketamine, and injected with P2 or control nanoparticles. The mice were sacrificed 30 minutes later, and the liver was harvested. 100-200 mg liver was homogenized; IRK was assayed in immunoprecipitates. The activity as measured in four livers of P2 injected and four control mice is shown.

FIG. 5, comprising FIG. 5A through FIG. 5C depicts results of experiments demonstrating P2 activates Akt.

FIG. 6, comprising FIG. 6A FIG. 6B depicts Phosphorylation of GSK3β in P2-stimulated cells. Identical samples to those in FIG. 6A were probed with anti-phospho-GSK3β-S9 antibody, followed by anti-GSK3β.

DETAILED DESCRIPTION

Figures 1A, 1B, 1C, 1D:
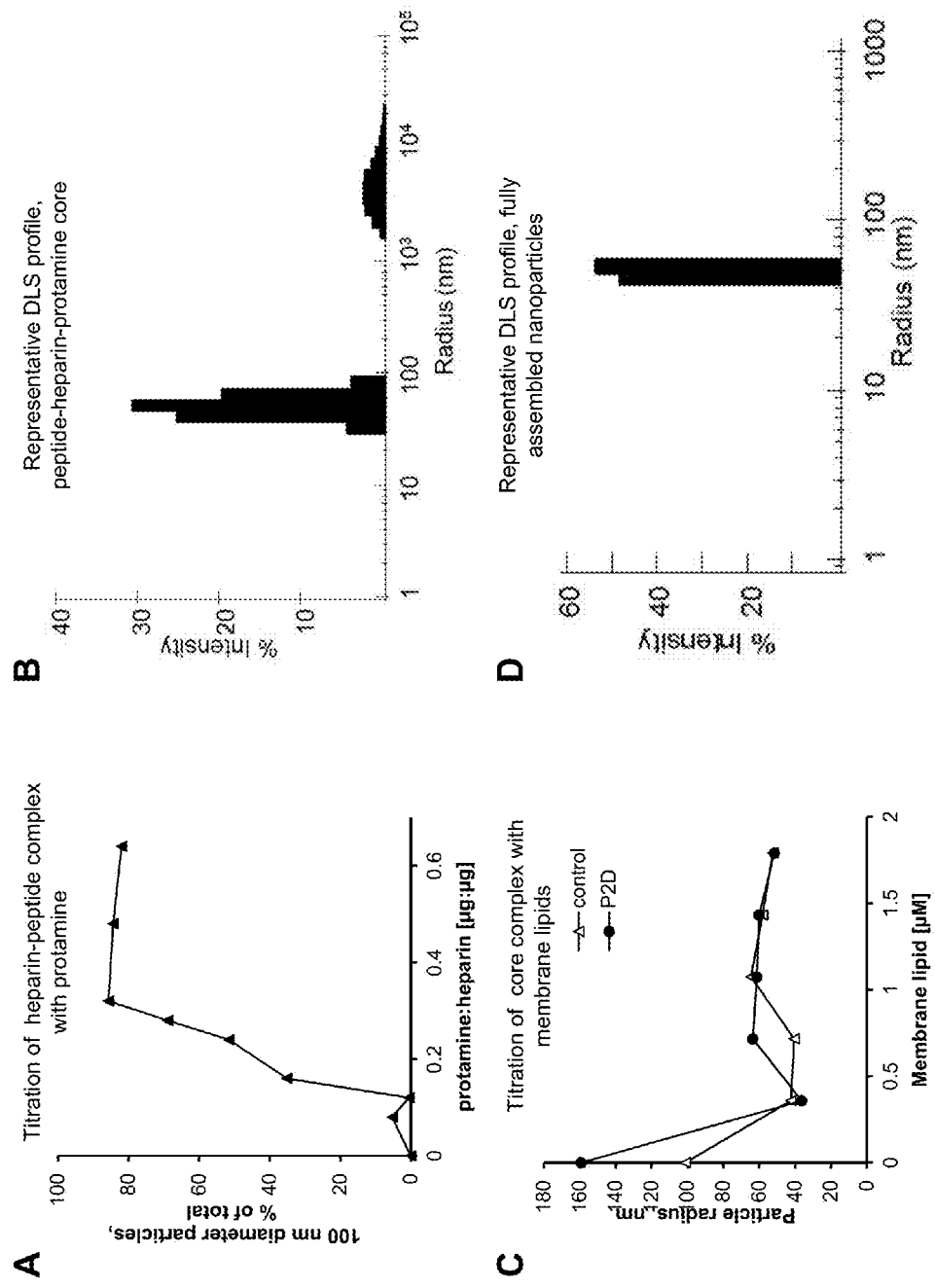
FIG. 1A depicts titration of heparin-peptide complex with protamine. Protamine samples (60 μl) containing 15 μg heparin and 200 nM peptide in PBS were tested for the particle hydrodynamic radius by dynamic light scattering (DLS). The proportion of particles with a radius of ~100 nm is plotted.
FIG. 1B depicts a representative DLS profile. The DLS profile of particles containing 0.3:1 protamine: heparin (w:w), together with 200 μM P2 (KYCCSRK (SEQ ID NO: 2)) is shown.
FIG. 1C depicts titration of core complex with membrane lipids. Core particles containing 0.3:1 protamine: heparin and increasing amounts of membrane particles prior to measurement of hydrodynamic radius by DLS.
FIG. 1D depicts a representative DLS profile of fully assembled nanoparticles. The DLS profile of particles containing 0.3:1 protamine: heparin after addition of 0.4 mM membrane lipid is shown.

In one aspect, the present invention provides a composition comprising an isolated peptide comprising a sequence of KRSCCYK (SEQ ID NO: 1). In one embodiment, the isolated peptide comprises D-amino acids. In one embodiment, the isolated peptide consists of D-amino acids. In certain embodiments, the isolated peptide and compositions of the invention may be used in the treatment or prevention of hyperglycemia or diseases or disorders related to hyperglycemia. In certain embodiments, the composition comprises a nanoparticle, wherein the isolated peptide comprising a sequence of SEQ ID NO: 1 is encapsulated within the nanoparticle.

In certain embodiments, the present invention provides methods for treating or preventing diabetes. For example, in certain embodiments, the method comprises administering an effective amount of a composition comprising an isolated peptide comprising a sequence of SEQ ID NO: 1. In one embodiment, the method further comprises administering a second therapeutic agent. Examples of additional therapeutic agents include anti-diabetic agents such as insulin.

Definitions

Unless defined otherwise, all technical and scientific terms used herein have the same meaning as commonly understood by one of ordinary skill in the art to which this invention belongs. Any methods and materials similar or equivalent to those described herein can be used in the practice or testing of the present invention.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal, or cells thereof whether in vitro or in situ, amenable to the methods described herein. In some embodiments, the patient, subject or individual is a mammal such as a non-primate (e.g., cows, pigs, horses, cats, dogs, rats, etc.) and a primate (e.g., monkey and human), most preferably a human. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based, in part, on the discovery that the a peptide comprising a sequence of KRSCCYK (SEQ ID NO:1) stimulates glucose uptake, improves hyperglycemia and stimulates the IRK/Akt/GSK pathway.

In one embodiment, the invention provides an isolated peptide comprising an amino acid sequence of SEQ ID NO: 1, wherein one or more amino acids of the peptide is in D configuration (D-amino acid). In some embodiments, the peptide further comprises modifications on the N-terminus, the C-terminus, or both. For example, in one embodiment, the peptide further comprises an acetyl group on the N-terminus. In another embodiment, the peptide further comprises an amido on the C-terminus.

The present invention is also based, in part, on the discovery that a nanoparticle encapsulating a peptide having a sequence of KRSCCYK (SEQ ID NO: 1) stimulates glucose uptake, improves hyperglycemia and stimulates the IRK/Akt/GSK pathway. Thus, the present invention also provides a composition comprising an isolated peptide comprising the amino acid sequence of SEQ ID NO: 1. In some embodiments, the composition further comprises a pharmaceutically acceptable carrier. In one aspect, the composition is in a form of a nanoparticle comprising a core and a membrane. In one embodiment, the nanoparticle core includes heparin, protamine and the peptide. In another embodiment the weight ratio of protamine to heparin is about 0.3:1 to about 0.6:1. In some embodiments, the nanoparticle has a membrane comprising cholesterol and DOTAP.

The present invention also provides methods for treating diabetes in a subject. In one embodiment, the method comprises administering an effective amount of an isolated peptide as described herein. It is also described herein that the isolated peptide and compositions of the invention stimulate glucose uptake and that when given in combination with insulin, glucose uptake is further increased. Thus, in some embodiments, the method further comprises administering a second therapeutic. In one embodiment, the second therapeutic is an anti-diabetic agent. In another embodiment, the second therapeutic is insulin.

Compositions

In one aspect, the present invention provides isolated peptides and compositions for treating diabetes. For example, in certain instances the compositions improve glucose tolerance. In some instances, the compositions lower blood glucose levels by increasing glucose uptake and suppress glucose-stimulated insulin secretion.

In one embodiment, the isolated peptide comprises an amino acid sequence of SEQ ID NO: 1. In some embodiments, the isolated peptide comprises D-amino acids. In one embodiment, each amino acid in the isolated peptide is a D-amino acid. In one embodiment, the isolated peptide further comprises an acetyl group on the N-terminus. In another embodiment, the isolated peptide further comprises an amido group on the C-terminus. In yet another embodiment, the isolated peptide further comprises an acetyl group on the N-terminus and an amido group on the C-terminus.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The invention should also be construed to include any form of a peptide having substantial homology to SEQ ID NO: 1. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to SEQ ID NO: 1.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to stimulate the differentiation of a stem cell into the osteoblast lineage. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of SEQ ID NO: 1.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides comprising an amino acid sequence of SEQ ID NO: 1 fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue (e.g., bone, regenerating bone, degenerating bone, cartilage). A targeting domain may target the peptide of the invention to a cellular component.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain a peptide comprising SEQ ID NO: 1 fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad. Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

In one embodiment, the present invention provides a composition comprising an isolated nucleic acid encoding SEQ ID NO: 1, or a biologically functional variant thereof.

Further, the invention encompasses an isolated nucleic acid encoding a peptide having substantial homology to SEQ ID NO:1. In certain embodiments, the isolated nucleic acid sequence encodes a peptide having at least 75%, 80%, 85%, 90%, 95%, 96%, 97%, 98%, or 99% sequence homology with SEQ ID NO: 1.

The isolated nucleic acid sequence encoding a peptide comprising SEQ ID NO: 1 can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding a peptide comprising SEQ ID NO: 1, or functional variant thereof. In one embodiment, the composition comprises an isolated RNA molecule encoding a peptide comprising SEQ ID NO: 1, or a functional variant thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, NH2, NHR, NR2 or ON, wherein R is C1-C6 alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding a peptide comprising SEQ ID NO: 1 is typically achieved by operably linking a nucleic acid encoding a peptide comprising SEQ ID NO: 1 or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a peptide comprising SEQ ID NO: 1, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Nanoparticles

In one embodiment, delivery of a peptide of comprises any suitable delivery method. In certain embodiments, delivery of a peptide can be achieved through a liposome, nanoparticle, micelle, dendrimer, microspheres, microparticles, nanoparticles, polymerosomes, and the like.

Thus, in one embodiment, the present invention provides a composition comprising a delivery vehicle comprising a peptide comprising SEQ ID NO: 1, or a nucleic acid molecule encoding a peptide comprising SEQ ID NO: 1. Exemplary delivery vehicles include, but are not limited to, microspheres, microparticles, nanoparticles, polymerosomes, liposomes, and micelles. For example, in certain embodiments, the delivery vehicle is loaded with a peptide comprising SEQ ID NO: 1, or a nucleic acid molecule encoding a peptide comprising SEQ ID NO: 1. In certain embodiments, the delivery vehicle provides for controlled release, delayed release, or continual release of its loaded cargo. In certain embodiments, the delivery vehicle comprises a targeting moiety that targets the delivery vehicle to a treatment site.

Liposomes, in one embodiment, increase intracellular stability, increase uptake efficiency and improve biological activity. In another embodiment, liposomes are hollow spherical vesicles composed of lipids arranged in a similar fashion as those lipids which make up the cell membrane. They have, in another embodiment, an internal aqueous space for entrapping water-soluble compounds and range in size from 0.05 to several microns in diameter. In another embodiment, liposomes can deliver peptides to cells in a biologically active form.

In one embodiment, the composition comprises a lipid nanoparticle (LNP) and one or more nucleic acid molecules described herein. For example, in one embodiment, the composition comprises an LNP and one or more peptides.

The LNP may comprise any lipid capable of forming a particle to which the one or more nucleic acid molecules are attached, or in which the one or more nucleic acid molecules are encapsulated. The term "lipid" refers to a group of organic compounds that are esters of fatty acids and are characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

In one embodiment, the LNP comprises one or more cationic lipids, and one or more stabilizing lipids.

In one embodiment, the LNP comprises a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids. In certain embodiments, the cationic lipid comprises a zwitterionic lipid that assumes a positive charge on pH decrease.

In certain embodiments, the cationic lipid comprises any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl)cholesterol (DC-Chol), N-(1-(2,3-dioleoyloxy)propyl)-N-2-(sperminecarboxamido)ethyl)-N, N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In one embodiment, the cationic lipid is an amino lipid. Representative amino lipids include, but are not limited to, 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanediou (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

In certain embodiments, the cationic lipid is present in the LNP in an amount from about 30 to about 95 mole percent. In one embodiment, the cationic lipid is present in the LNP in an amount from about 30 to about 70 mole percent. In one embodiment, the cationic lipid is present in the LNP in an amount from about 40 to about 60 mole percent. In one embodiment, the LNP comprises only cationic lipids.

In certain embodiments, the LNP comprises one or more additional lipids which stabilize the formation of particles during their formation.

Suitable stabilizing lipids include neutral lipids and anionic lipids.

The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydro sphingomyelins, cephalins, and cerebrosides.

Exemplary neutral lipids include, for example, distearoyl-phosphatidylcholine (DSPC), dioleoylphosphatidylcholine (DOPC), dipalmitoylphosphatidylcholine (DPPC), dioleoyl-phosphatidylglycerol (DOPG), dipalmitoylphosphatidyl-glycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). In one embodiment, the neutral lipid is 1,2-distearoyl-sn-glycero-3-phosphocholine (DSPC).

The term "anionic lipid" refers to any lipid that is negatively charged at physiological pH. These lipids include phosphatidylglycerol, cardiolipin, diacylphosphatidylserine, diacylphosphatidic acid, N-dodecanoylphosphatidylethanolamines, N-succinylphosphatidylethanolamines, N-glutaryl-phosphatidylethanolamines, lysylphosphatidylglycerols, palmitoyloleyolphosphatidylglycerol (POPG), and other anionic modifying groups joined to neutral lipids.

In certain embodiments, the LNP comprises glycolipids (e.g., monosialoganglioside $GM_1$). In certain embodiments, the LNP comprises a sterol, such as cholesterol.

In certain embodiments, the LNP comprises an additional, stabilizing-lipid which is a polyethylene glycol-lipid. Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol)$_{2000}$)carbamyl]-1,2-dimyristyloxlpropyl-3-amine (PEG-c-DMA). In one embodiment, the polyethylene glycol-lipid is PEG-c-DOMG).

In certain embodiments, The additional lipid is present in the LNP in an amount from about 1 to about 10 mole percent. In one embodiment, the additional lipid is present in the LNP in an amount from about 1 to about 5 mole percent. In one embodiment, the additional lipid is present in the LNP in about 1 mole percent.

In certain embodiments, the LNP comprises one or more targeting moieties which are capable of targeting the LNP to a cell or cell population. For example, in one embodiment, the targeting moiety is a ligand which directs the LNP to a receptor found on a cell surface.

In certain embodiments, the LNP comprises one or more internalization domains. For example, in one embodiment, the LNP comprises one or more domains which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo.

In one certain embodiments, a peptide comprising SEQ ID NO: 1 is encapsulated in a nanoparticle. In one embodiment the nanoparticle comprises a core and a membrane. In one embodiment the nanoparticle has a core comprising the peptide of the invention, heparin, and protamine. In some embodiments, the weight ratio of protamine to heparin is about 0.3:1 to about 0.6:1. In certain embodiments, the nanoparticle comprises about 250 µg/ml heparin, 200 nM peptide and 75 µg/ml protamine. In another embodiment, the nanoparticle membrane comprises cholesterol and DOTAP. In another embodiment, the amount of cholesterol and the amount of DOTAP in the nanoparticle membrane are equimolar.

Treatment Methods

The present invention provides a method for the treatment or prevention of a condition associated with hyperglycemia, impaired glucose uptake from circulation or abnormal insulin cascade, in a subject in need thereof. Exemplary conditions treated or prevented by way of the present invention include, but are not limited to, diabetes or pre-diabetes. In one embodiment, the condition is Type 1 diabetes. In another one embodiment, the condition is Type 2 diabetes.

In certain embodiments, the method comprises administering an effective amount of a peptide or a composition described herein to a subject diagnosed with, suspected of having, or at risk for developing diabetes. Thus, the present invention relates to the prevention and treatment of a disease or disorder by administration of a therapeutically effective amount of a peptide comprising SEQ ID NO: 1, or a composition comprising said peptide, to a subject in need thereof, for the treatment or prevention of a disease or disorder characterized by hyperglycemia, including but not limited to diabetes. In some embodiments, the peptide comprises D-amino acids. In one embodiment, each amino acid in the peptide is a D-amino acid. In one embodiment, the peptide further comprises an acetyl group on the N-terminus. In another embodiment, the peptide further comprises an amido group on the C-terminus. In yet another embodiment, the peptide further comprises an acetyl group on the N-terminus and an amido group on the C-terminus.

One skilled in the art, based upon the disclosure provided herein, would understand that the invention is useful in subjects who, in whole (e.g., systemically) or in part (e.g., locally, tissue, organ), are being or will be, treated for a disease or disorder associated with hyperglycemia. The skilled artisan will appreciate, based upon the teachings provided herein, that the diseases and disorders treatable by the compositions and methods described herein encompass any disease or disorder where a peptide comprising SEQ ID NO: 1 will promote a positive therapeutic outcome.

In certain aspects, the peptide or the composition is contacted to a cell or tissue where diseased glucose uptake is impaired. In one embodiment, the composition is administered systemically to the subject.

The peptide or the composition of the invention may be administered to a patient or subject in need in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

In certain embodiments, the peptide or the composition of the invention is administered in combination with one or more additional therapeutic agents. For example, the composition of the invention may be administered with anti-diabetic agents. In one embodiment, the peptide or the composition of the invention is administered in combination with insulin.

In one embodiment, the method comprises administering to the subject a nanoparticle comprising a peptide comprising SEQ ID NO: 1 or a nucleic acid encoding a peptide comprising SEQ ID NO: 1. In some embodiments, the peptide comprises D-amino acids. In one embodiment, each amino acid in the isolated peptide is a D-amino acid. In one embodiment, the peptide further comprises an acetyl group on the N-terminus. In another embodiment, the peptide further comprises an amido group on the C-terminus. In yet another embodiment, the peptide further comprises an acetyl group on the N-terminus and an amido group on the C-terminus.

In another embodiment, the method comprises administering to the subject a composition comprising a peptide comprising SEQ ID NO: 1, wherein the peptide comprises at least one D-amino acid. In another embodiment, each amino acid in the peptide is a D-amino acid. In some embodiments, the peptide comprises D-amino acids. In one embodiment, each amino acid in the isolated peptide is a D-amino acid. In one embodiment, the peptide further comprises an acetyl group on the N-terminus. In another embodiment, the peptide further comprises an amido group on the C-terminus. In yet another embodiment, the peptide further comprises an acetyl group on the N-terminus and an amido group on the C-terminus.

In one embodiment, the method comprises administering to the subject a scaffold comprising a peptide comprising SEQ ID NO: 1, or a cell modified to express a peptide comprising SEQ ID NO: 1. In some embodiments, the peptide comprises D-amino acids. In one embodiment, each amino acid in the isolated peptide is a D-amino acid. In one embodiment, the peptide further comprises an acetyl group on the N-terminus. In another embodiment, the peptide further comprises an amido group on the C-terminus. In yet another embodiment, the peptide further comprises an acetyl group on the N-terminus and an amido group on the C-terminus.

Subjects to which administration of the peptide or the composition of the invention is contemplated include, but are not limited to, humans and other primates, mammals including commercially relevant mammals such as non-human primates, cattle, pigs, horses, sheep, cats, and dogs.

The peptide or the composition of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the peptide or the composition may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are preferably administered by i.v. injection.

Methods of treatment of the diseases encompassed by the invention can comprise the transplantation of single cells, cell lines, compositions, or cell populations of the invention into a subject in need thereof. In certain embodiments, the subject is a human.

Pharmaceutical Composition and Administration

The isolated peptides and compositions of the invention can be formulated and administered to a subject. For example, peptides comprising SEQ ID NO:1 can be formulated and administered to a subject for the treatment and/or prevention of a disease or disorder.

The present invention also provides pharmaceutical compositions comprising one or more of the compositions described herein. In some aspects, the invention encompasses the preparation and use of pharmaceutical compositions comprising a peptide of SEQ ID NO: 1 as an active ingredient for the treatment or prevention of a disease or disorder, including but not limited to, diabetes. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para hydroxybenzoates, ascorbic acid, and sorbic acid.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

Pharmaceutical compositions that are useful in the methods of the invention may be prepared, packaged, or sold in formulations suitable for oral, rectal, vaginal, parenteral, topical, pulmonary, intranasal, buccal, intravenous, transdermal, subcutaneous, intramuscular, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Typically dosages of the compound of the invention which may be administered to an animal, preferably a human, range in amount from about 0.01 mg to about 1000 mg per kilogram of body weight of the animal. The precise dosage administered will vary depending upon any number of factors, including, but not limited to, the type of animal and type of disease or disorder being treated, the age of the animal and the route of administration. Preferably, the dosage of the compound will vary from about 1 mg to about 100 mg per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease or disorder being treated, the type and age of the animal, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Nanoparticle Delivered Human Biliverdin Reductase-Based Peptide Increases Glucose Uptake by Activating IRK/Akt/GSK3 Axis: the Peptide is Effective in the Cell, Wild-Type and Diabetic Ob/Ob Mice The N-myristoylated form of $K^{291}$YCCSRK (SEQ ID NO: 2) (P2) synthesized with the naturally occurring L-enantiomeric amino acids stimulates glucose uptake in several cell types. P2 is membrane permeable and effective for a brief period in the cultured cells. However, this composition is unsuitable for use as a therapeutic agent as small molecules (MW <5 kDa) are rapidly depleted in the circulation and excreted via the kidneys, and L-amino acid peptides are highly susceptible to proteolytic degradation. Accordingly, described herein is a nanoparticle formulation of P2 containing the peptidase-resistant D-enantiomeric form of P2 (P2D). The data presented herein demonstrates that P2D is more effective in increasing glucose uptake by cultured cells than myristoylated P2, and decreased glucose level in mice. Experiments presented herein were conducted to examine IRK activity, glucose uptake and whether modulation of IRK activity and glucose uptake involves Akt/GSK pathway. It is described herein that the construct is effective in ameliorating hyperglycemia and in stimulating the IRK/Akt/GSK axis. The mechanism is demonstrated to be that predicted for activation of IRK.

The materials and methods employed in these experiments are now described.

Materials

Peptides with all D-amino acids—Ac-KRSCCYK-NH2 (SEQ ID NO: 1), Ac-YKCKCRS-NH2 (SEQ ID NO: 3)—and myristoylated peptides were synthesized by EZ Biolabs (Carmel, Ind.). Heparin (porcine) was obtained from Thermo-Fisher, protamine was from EMD-Calbiochem, 1,2-dioleoyl-3-trimethylammonium-propane chloride (DOTAP) was from Avanti Polar Lipids (Alabaster, Ala.) and cholesterol (>99% purity) was from Sigma-Aldrich. Insulin receptor β-subunit (IRK), IGF receptor β-subunit (IGFR kinase), IRS and IRS Y608 peptide substrate were from Enzo Life Sciences (Farmingdale, N.Y.), [γ-32P]-ATP was from Perkin-Elmer and [1-3H]-2-deoxyglucose was from Amersham. Antibodies were obtained from Cell Signaling (Beverly, Mass.).

Peptides

Myristoylated peptides were synthesized with L-amino acids. The peptides were as follows: P2, myr-KYCCSRK (SEQ ID NO: 2); P2sc, myr-SRCKCKY (SEQ ID NO: 4); control, peptide (a) myr-KKRILHC (SEQ ID NO: 5); peptide (b) myr-KRNRYLSF (SEQ ID NO: 6). Two peptides contained only D-amino acids, DP2 Ac-KRSCCYK-NH2 (SEQ ID NO: 1); and D control Ac-YKCKCRS-NH2 (SEQ ID NO: 3).

Preparation of Nanoparticles

Nanoparticle assembly was based on a previously described method (Kim and Huang, 2012, J Control Release 157:279-86). Membrane lipids were prepared from a 2 ml solution of 18 mM DOTAP and 18 mM cholesterol in 3:1 chloroform: methanol. The solvent was evaporated under constant airflow, followed by vacuum drying overnight. The lipids were then slowly suspended in 2 ml PBS, and the suspension was stored at −20° C. Unilamellar membranes were prepared by extrusion of the lipid stock through a 100 nm filter, and were used within one week. Heparin (2.5 mg/ml) and protamine (2.0 mg/ml) stocks were prepared in 20 mM Hepes, pH 7.5 and filter sterilized (0.2 µm). Peptides were dissolved in PBS at 2 mM. In initial experiments, peptide and heparin were combined (1:1 v:v), after which increasing amounts of protamine stock were added, and the volume was adjusted to yield a final peptide concentration of 200 nM. The particle sizes were determined by dynamic light scattering (DLS) using a Dynapro II plate reader (Wyatt Instruments, Goleta, Calif.). The particle core formulation for subsequent experiments was based on these data: cores consisted of 250 µg/ml heparin, 200 nM peptide and 75 µg/ml protamine. The core particles were titrated with membranes (hydrodynamic radius of ~100 nm by DLS), and the size again was assessed by DLS.

Cell Culture and Transfection

Cultures of HEK293 were maintained in DMEM with 10% FBS. Cells were starved overnight in medium with 0.1% FBS. When used, insulin was added to serum-starved cultures at 100 nM. Human skeletal muscle cells were maintained in 1:1 DMEM:F12 medium containing 15% FBS. One day prior to glucose uptake analysis, the medium was changed to low glucose (5 mM) DMEM with 10% FBS.

Glucose Uptake in Cells

Glucose uptake was assessed using 2-deoxy 1-[$^3$H] glucose as described previously (Lerner-Marmarosh et al., 2005, PNAS 102:7109-14), with modification. Cells in 24 well plates were grown to near confluence, and starved in glucose-free DMEM (Invitrogen) containing 1 mg/ml BSA for 2 hours. Peptides (20 µM) were added and incubation continued for the indicated times, followed by treatment with 100 nM insulin 15 minutes. Deoxyglucose (0.2 mM, containing 1 µCi/ml [3H]-deoxyglucose) was added for 15 minutes. Cells were washed 3 times with cold PBS and solubilized in 150 µl 50 mM NaOH. Radioactivity was measured and normalized to protein concentration. Assessments were made in triplicate and experiments were repeated three times.

Akt and GSK3 Activation

HEK cells were incubated in low glucose DMEM with 0.1% FBS, overnight. Cells were treated with 40 µM myristoylated peptide for a total of 15 min; insulin or IGF-1, if used, were included for the final 10 minutes. Cells were harvested, lysed in buffer with triton ×100, and whole cell lysates were analyzed for phosphorylated Akt ($T^{308}$, $S^{473}$) or GSK3 ($\alpha$-$S^{21}$, $\beta$-$S^9$) species by Western blotting. Each blot was stripped and probed with anti-Akt1 or anti GSK3$\alpha$ or GSK3$\beta$ antibody, as appropriate, to control for loading.

Kinase Assays

Purified IRK was assayed as previously (Lerner-Marmarosh et al., 2005, PNAS 102:7109-14), using 300 µM IRS-1 Y608 peptide substrate. IRK autophosphorylation was determined as described earlier (Gibbs et al., 2012, J Biol Chem 287:1066-79). hBVR-based peptides (20 µM) were added as activators or inhibitors. In some experiments, the hBVR-based peptides were themselves used as substrates. Incorporation of $^{32}$P was determined by liquid scintillation counting. For IRK assays in cells or tissue samples, the protein was solubilized in buffer containing triton ×100 and DTT and immunoprecipitated with antibody to IR β-chain. Immunoprecipitates bound to protein A/G-agarose were washed in lysis buffer, followed by IRK assay buffer, and kinase activity was measured as before (Lerner-Marmarosh et al., 2005, PNAS 102:7109-14). Akt kinase activity was measured in 20 mM HEPES, pH7.4, 50 mM MgCl2, 0.5 mM EGTA, 2 mM DTT, 100 µM ATP (5 nmole, containing 10 µCi [γ$^{32}$P]-ATP) with 30 µM Crosstide (GRPRTSS-FAEGKK (SEQ ID NO: 7)) substrate; incorporated $^{32}$P was measured as above.

Animal Studies

C57BL/6J and homozygous Ob/Ob mutant mice with the same genetic background were obtained from Jackson Laboratories. For glucose tolerance tests, wt mice were deprived of food for 12 hours prior to the experiment. Mice were anesthetized with subcutaneous ketamine (150 mg/kg). In some experiments ketamine-xylazine (80, 4 mg/kg, resp.) was used, but this was discontinued due to the hyperglycemia induced by xylazine (Saha et al., 2005, exp Biol Med 230:777-84). Blood was obtained from the tail, and the blood glucose was measured using a portable glucometer (Contour, Bayer, Mishawaka, Ind.) prior to injection. Nanoparticles (1.1 µg/g peptide) were injected intraperitoneally, followed 10 minutes later by injection with glucose (1.5 mg/g, ip.). Blood was collected at intervals after administration of glucose, and the blood glucose was measured; at least two readings were made at each time point. Glucose stimulation of insulin secretion was measured in mice treated with P2 or control nanoparticles. Prior to injection with particles, ~25 µl of blood was collected into tubes containing 2.5 µl 50 mM EDTA in PBS. Ten minutes after injection of nanoparticles (1.1 µg/g), glucose (0.5 mg/g body weight) was administered ip., after which blood was collected at 2, 5 and 10 minutes to measure glucose-stimulated insulin secretion (Favelyukis et al., 2001, Nat Struct Biol 8:1058-63; insulin levels in 5 µl whole blood was determined by ELISA (Alpco, Salem N.H.).

Statistical Analysis

Besides animal studies all experiments were performed at least three times. Statistical analysis by one-way ANOVA and non-linear regression were performed using Prism software.

The results of the experiments are now described.

Although they have advantages over small molecules in that they have a higher affinity/specificity to target and lower toxicity in the intact body, peptides exhibit a short dwell time due to both rapid renal clearance and lack of stability due to protease degradation. Furthermore, peptides have limited access to intracellular space. In order to reduce degradation by serum and tissue peptidases in vivo, chemical alterations of peptides are necessary, such as the use of non-natural D-amino acids, which substantially prevents peptide degradation, as they are poorly recognized by peptidases. The purpose of this study was to develop a means of delivering the biologically active peptide to animals, in a form that would allow it to persist in the organism. The modified peptide was synthesized using D-amino acids with reversed sequence to maintain the secondary structure. Furthermore, both the N- and C-termini were blocked, using acetyl and amido groups, respectively (Sato et al., 2006, Curr Opin Biotechnol 17:638-42; McGregor, 2008, Curr Opin Pharmacol 8:616-9). Because, in general, the size of particles is inversely proportional to its clearance time from circulation, it was also essential that the mode of delivery be modified, to protect the peptide against such rapid loss. To this end, particles ~100 nm in diameter were used, which should persist in the circulation long enough to reach target cells. Lipid-encapsulated particles that are relatively homogeneous in size and carry a net positive charge should facilitate uptake by cells.

Characterization of Nanoparticles

The first stage was construction of a suitably sized core containing peptide, heparin and protamine (Kim and Huang, 2012, J Control Release 157:279-86). Initially, a stock containing heparin and peptide was titrated with protamine, and the resulting material was analyzed by dynamic light scattering (FIG. 1A). At low protamine:heparin ratios, the particles were generally small and heterogeneous in size. However, at a ratio of 0.3:1, approximately 80-90% of the particles had a hydrodynamic radius of approximately 80-100 nm (FIG. 1B). No further increase in the proportion of particles in this size class was seen at higher concentrations of protamine; in some instances, there was a tendency for larger aggregates to form. These data enabled construction of a standardized core that contained 250 µg/ml heparin, 200 nM peptide, and 75 µg/ml protamine. Unilamellar membranes, containing an equimolar ratio of cholesterol and DOTAP, were prepared by extrusion through a 0.1 µm filter. The resulting membrane particles had a mean hydrodynamic radius of 100 nm, as measured by DLS. Core particles, prepared as above, were then titrated with membranes (FIG. 1C); the control particles in this experiment contained 250 µg/ml heparin and 90 µg/ml protamine, with no P2. Addition of 0.4 µM membrane to the core particles yielded a homogeneous distribution of particles with a hydrodynamic radius of ~50 nm (FIG. 1D).

D-Peptide Nanoparticles Potentiate Glucose Uptake

Figures 2A, 2B, 2C:
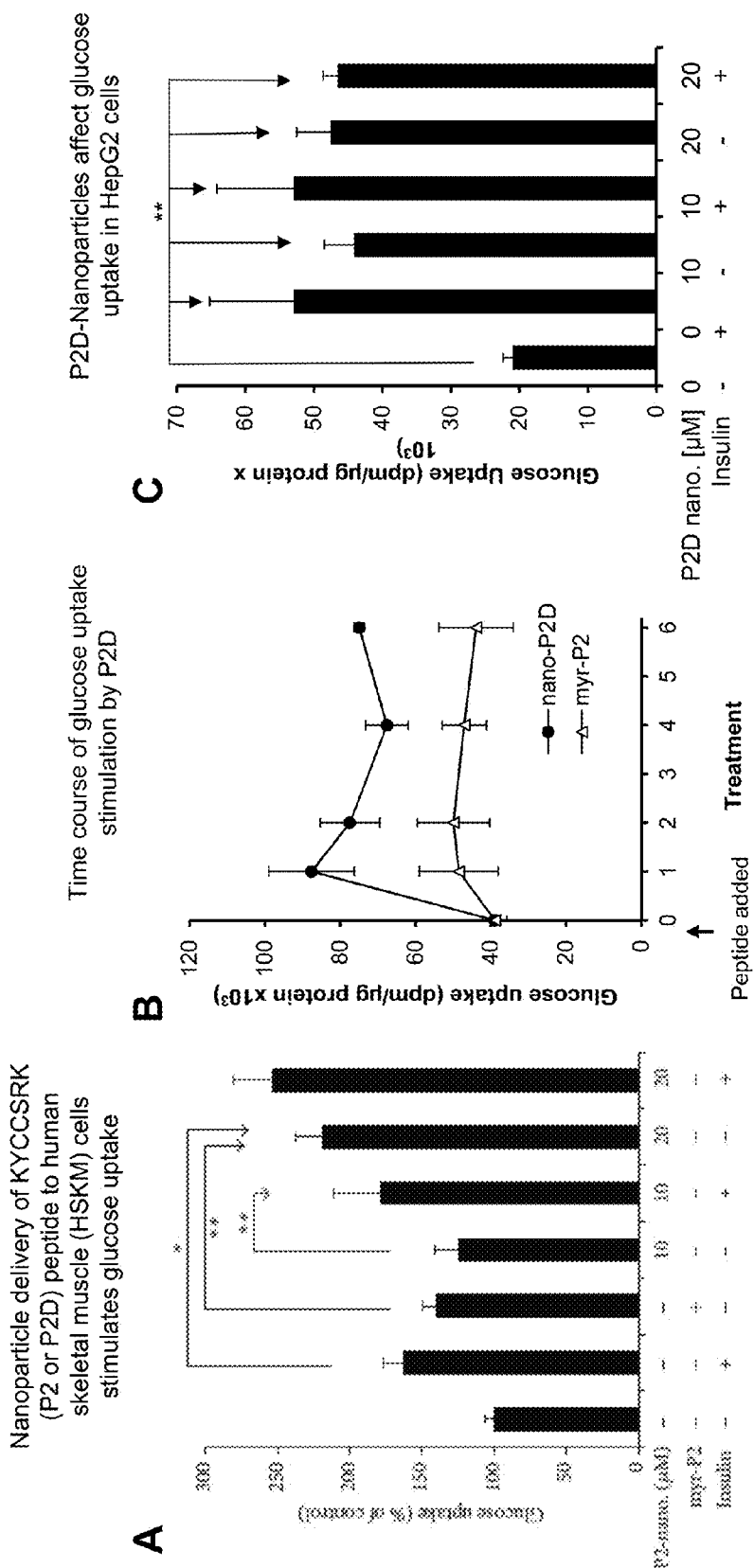
FIG. 2A depicts Nanoparticle delivery of peptide P2 to human skeletal muscle (HSKM) cells stimulates glucose uptake. HSKM cells were grown in low glucose, low FBS medium overnight, then media was replaced with PBS containing 1% BSA for 1 h. Cells were pretreated for 2 hours with 20 μM myristoylated P2 or with 10 or 20 μM P2-nanoparticles, followed by measuring 3H-deoxyglucose uptake over a 15 minutes interval. Insulin, when used, was added at the same time as 3H-deoxyglucose. * P<0.05,  P<0.01.
FIG. 2B depicts a time course of glucose uptake stimulation by P2. HSKM cells were starved overnight as in described in FIG. 2A. Medium was changed to glucose-free DMEM with 1% BSA for 1 hour prior to treatment with 20 μM myr-P2 or with P2-nanoparticles for the indicated times. Glucose uptake was measured as in A.
FIG. 2C** depicts P2-nanoparticles affect glucose uptake in HepG2 cells. HepG2 cells were starved in low glucose DMEM with 0.1% FBS overnight. Treatment with peptide nanoparticles was for 1 h. Glucose uptake was measured as described in FIG. 2A.

P2 is known to stimulate glucose uptake, whether it is delivered as myr-P2 or if it is expressed in cells transfected with a suitable expression plasmid (Gibbs et al., 2014, FASEB J 28:2478-91). The nanoparticle delivery system was compared with myristoylated peptide for its effect on glucose uptake by cultured cells. Cells were treated with peptide for 2 hours, after which glucose uptake was measured (FIG. 2A). It was apparent that myr-P2 and insulin stimulated glucose uptake to about the same extent, whereas the nanoparticles were significantly more effective. The lower dose of P2D-nanoparticles tested did not effectively increase glucose uptake, although the lower dose combined with insulin was more effective than either low dose peptide or insulin alone (FIG. 2A). The distinction was lost at higher peptide dose. Bearing in mind that the D-amino acid peptide was designed to be more stable in the intracellular environment, the data cannot distinguish between peptide delivery being more efficient and reduced turnover of peptide in the cells. In a second experiment, cells were treated with 20 µM myr-P2 or P2D-nanoparticles for times ranging from 1 to 6 hours, after which glucose uptake was measured. It is apparent from FIG. 2B that the nanoparticle treated cells showed enhanced glucose uptake at all times examined. It is also noted that the initial, albeit lesser, stimulation of glucose uptake by myr-P2 was effectively lost by 6 hours, indicating that the myr-P2 is less stable in the cell than the D-form P2D-nanoparticles. The effect of peptide was not cell-type specific, since HepG2 cells showed enhanced glucose uptake after treatment with peptide (FIG. 2C). In this experiment, however, the cells had been subjected to a longer period of serum deprivation than the skeletal muscle cells, which resulted in a more robust response to insulin.

P2D Nanoparticles Modulate Circulating Glucose Levels In Vivo

The experimental data above established that the nanoparticles deliver the active P2D to the cell, leading to increased uptake of glucose; confirming our earlier observations with P2 delivered as a myr-peptide or expressed in the cell. The current delivery system was designed to deliver the peptide to an intact animal and therefore its effect on circulating glucose was examined in normal mice subjected to a high dose of glucose, and in obese mice with high circulating glucose, or in response to a stress induces high blood glucose. First, the effect of nanoparticle-P2D on glucose clearance from the blood was examined using a glucose tolerance test. It was found that mice injected with P2D (as nanoparticles) 10 minutes prior to glucose cleared blood glucose much faster than their counterparts injected with a control peptide (FIG. 3A); the control peptide has the same amino acid composition but, an altered sequence. As noted in the figure, the P2D-injected mice showed significantly lower blood glucose than the controls at 30 and 60 minutes ($P<0.001$, $P<0.05$, respectively). P2D treatment is therefore driving rapid glucose clearance from the circulation.

Figures 3A, 3B, 3C, 3D:
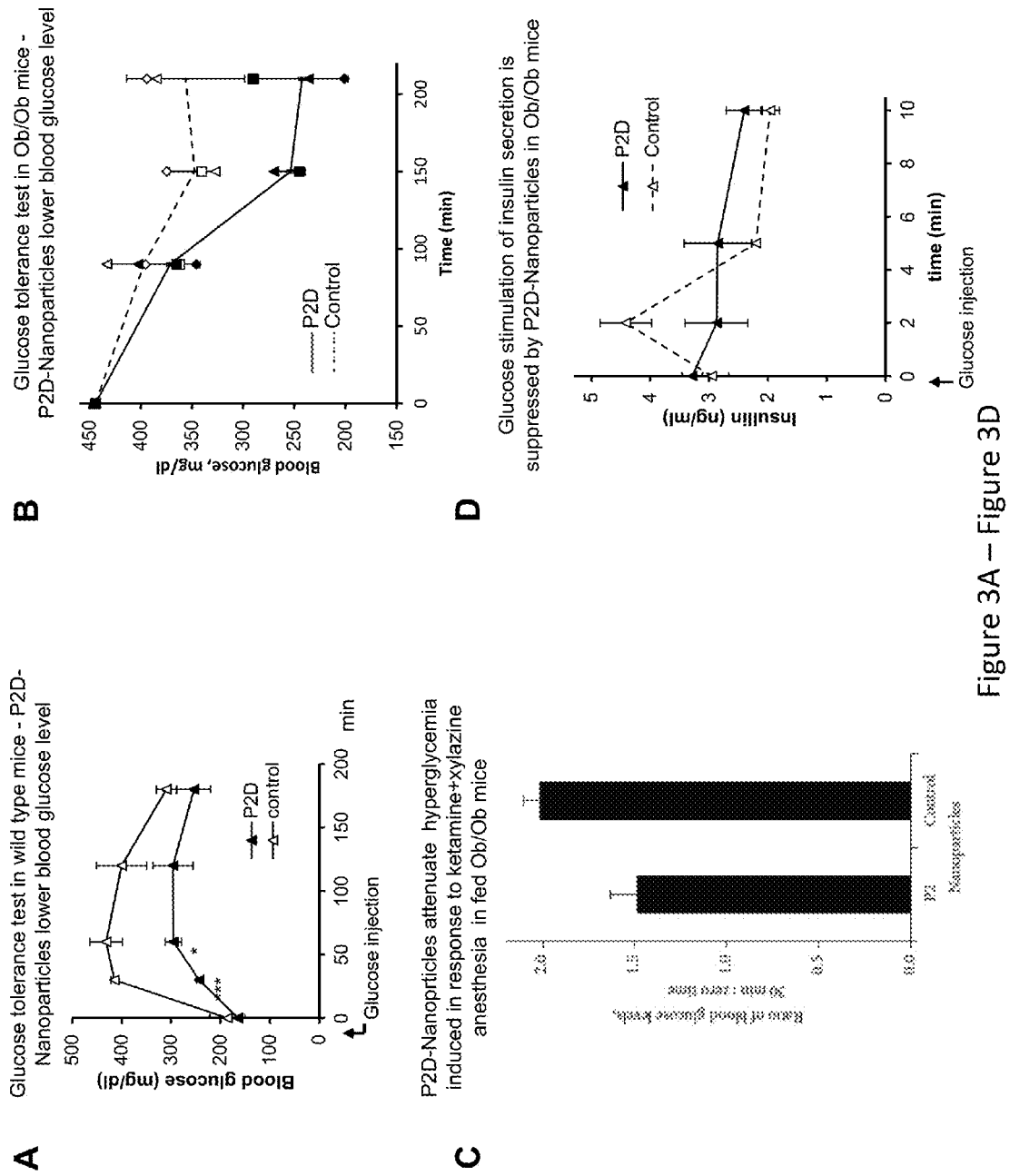
FIG. 3A depicts glucose tolerance test in wild type mice-P2-nanoparticles lower blood glucose level. C57B1/6J mice were deprived of food overnight. After anesthesia, P2 or control nanoparticles (1.1 µg peptide/g body weight) were injected i.p., followed by glucose injection 10 minutes later (1.5 mg/g body weight). Blood glucose was measured with a portable glucometer at the times shown. The values are mean±s.e.m. for four mice in each group. * P<0.05, *** P<0.001.
FIG. 3B depicts a glucose tolerance test in Ob/Ob mice. P2-nanoparticles lower blood glucose level. Anesthetized mice were injected with nanoparticles and blood glucose was measured starting 30 minutes later, for the times indicated in the figure. Data points are for individual mice: open symbols are controls (dashed line connects the mean for each time point); filled symbols and solid line represent P2-nanoparticle-injected animals.
FIG. 3C depicts P2-Nanoparticles attenuate hyperglycemia induced by ketamine-xylazine anesthesia in fed Ob/Ob mice. Blood was withdrawn for glucose measurement as soon as the mice became unconscious. Second sample was taken at 30 minutes after nanoparticle injection. Data for each mouse are presented as the ratio of blood glucose at 30 minutes to that at zero time. The difference in mean ratio is significant; *p<0.05.
FIG. 3D depicts glucose stimulation of insulin secretion is suppressed by P2-nanoparticles in Ob/Ob mice. Ob/Ob mice were injected with P2 or control nanoparticles, followed by glucose injection (0.5 mg/g body weight). Blood was withdrawn at the indicated times, and insulin was measured by ELISA. Open symbols are control mice; filled symbols are P2-nanoparticles treated mice.

Next, the effect of the peptide on glucose uptake from the circulation was examined in Ob/Ob mutant mice, as a model of Type II diabetes that had been fed ad libitum. In one experiment, the mice were injected with peptide nanoparticles, and blood glucose was monitored starting at 30 minutes after injection and continuing for a further 3.5 hours (FIG. 3B). The P2D injected mice showed a steady reduction in blood glucose levels over the course of the experiment. Glucose levels in mice injected with control particles also showed a time dependent decrease, but the rate and magnitude of decrease were lower. It has been reported by Saha et al. (Saha et al., 2005, Exp Biol Med 230:777-84) that ketamine-xylazine anesthesia induces hyperglycemia in experimental mice. The effect of P2D-nanoparticles was tested on this phenomenon. Peptide nanoparticles were injected into Ob/Ob mice when anesthesia was established. Comparison of blood glucose before and 30 minutes after injection with peptide (FIG. 3C) revealed that blood glucose in control-injected mice increased by a factor of 2.02±0.09, compared to only a 1.49±0.15 fold increase in the P2D-treated animals (P=0.02).

A rapid increase in blood glucose triggers insulin secretion, which in turn activates mechanisms for glucose uptake. Therefore it was tested whether P2D-nanoparticles affected the glucose-stimulated insulin secretion. The following experiment with the obese mice examined the stimulation of insulin secretion in response to glucose in control and P2D-treated mice. A modest stimulation of insulin secretion was seen in control animals (FIG. 3D). However, treatment with P2D 10 minutes prior to injection of glucose prevented glucose stimulation of insulin secretion. Taken together, the data suggest that P2D is an effective stimulator of glucose uptake from the circulation, ameliorating hyperglycemia and acting independently of insulin.

P2 Activation of IRK

Figures 4A, 4B, 4C, 4D, 4E:
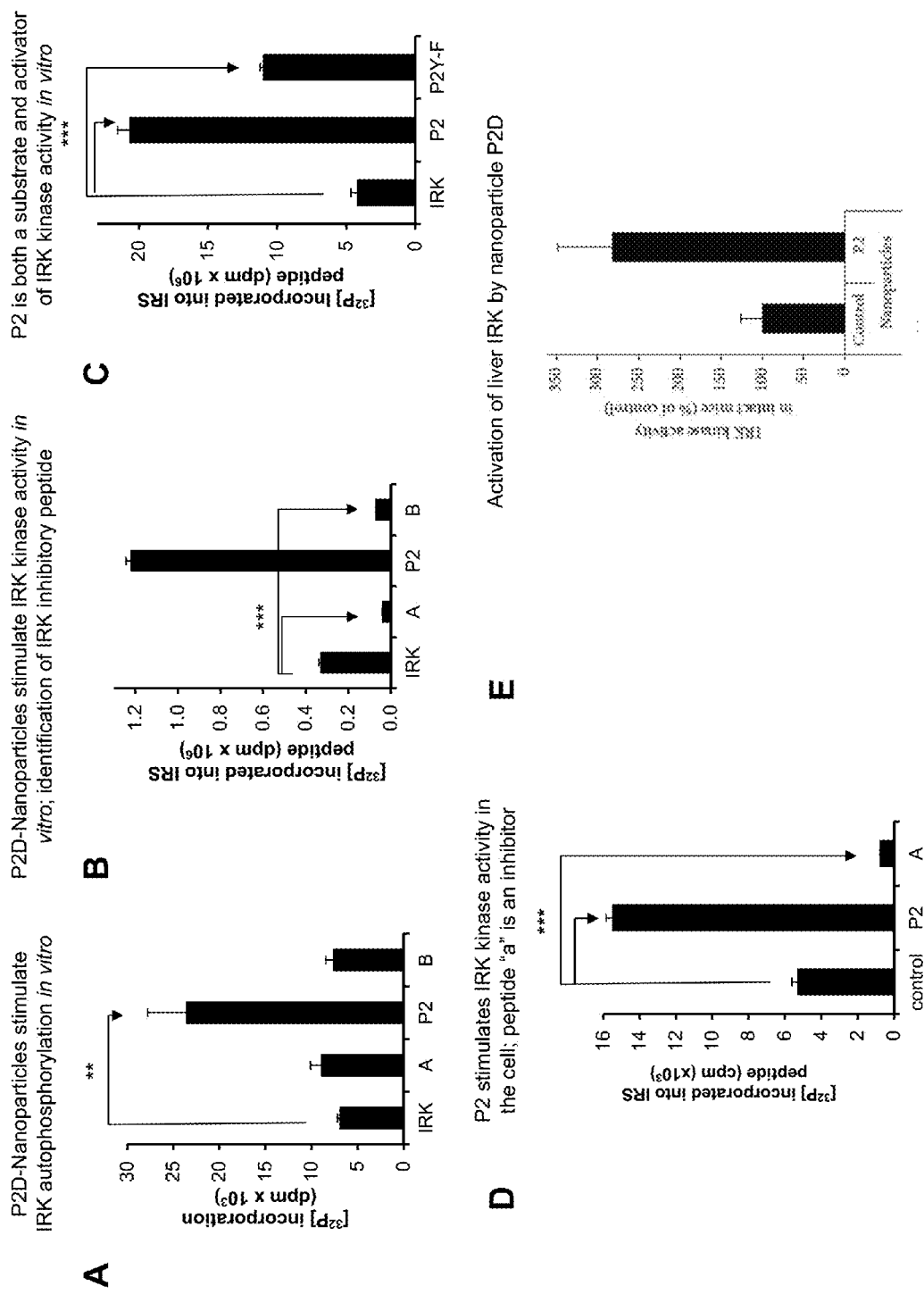
FIG. 4A through FIG. 4E, depicts results of experiments demonstrating P2 activation of IRK.

To elucidate the mechanism by which P2D-nanoparticles are acting the earlier observations that P2 is activating IRK was confirmed. First, P2 enhances the activity of IRK in an autophosphorylation reaction (FIG. 4A). It should be noted that IRK is a tyrosine kinase, and that P2 contains a tyrosine residue that is phosphorylated by IRK in full-length hBVR (Lerner-Marmarosh et al., 2005, PNAS 102:7109-14); it is therefore possible that the peptide is functioning as a substrate in this reaction. Inclusion of two other BVR based peptides ((a)—KKRILHC (SEQ ID NO: 5) and (b)—KRNRYLSF (SEQ ID NO: 6)) did not lead to increased [$^{32}$P] incorporation in this assay (FIG. 4A), suggesting specificity to P2 activation. Since increased IRK autophosphorylation results in increased kinase activity, the effect of P2 on IRK kinase activity towards an IRS peptide substrate was tested. As expected, inclusion of P2 led to an approximately four-fold increase in IRK-dependent incorporation of [$^{32}$P] into the peptide substrate when compared to IRK alone (FIG. 4B). In contrast, other BVR-based peptides (including those used in panel A) inhibited the kinase activity. Peptide (b) has previously been shown to inhibit insulin-dependent stimulation of glucose uptake (Gibbs et al., 2014, FASEB J 28:2478-91) and it is probable that it does so by inhibiting cellular IRK. The tyrosine residue in P2 appears to be necessary for complete activation; mutation of the residue to phenylalanine results in a significant decrease in substrate phosphorylation (FIG. 4C). These observations confirm and extend those made in an earlier study (Gibbs et al., 2014, FASEB J 28:2478-91).

Next, IRK activation was examined in cultured cells treated with myristoylated peptides. Cells were lysed 15 minutes after treatment with peptide and the IR β-chain was immunoprecipitated from the lysates. The kinase activity of the immunoprecipitated protein was measured using the IRS peptide substrate. The findings parallel those seen in the in vitro assay, in that P2 activated IRK approximately 3-fold in the cell (FIG. 4D), while peptide (a) was a potent inhibitor of the kinase.

To test whether the same activation was seen in vivo, C57B1/6J mice were injected with P2D- or control nanoparticles. They were sacrificed 30 minutes after injection, and the livers were harvested. Liver IRK was isolated from homogenates by immunoprecipitation with antibody against the IR β-chain, and kinase activity in the immunoprecipitates was determined. The IRK activity of individual mice is shown in FIG. 4E. It is apparent that there is variation between individual animals. In general, the mice injected with P2D-nanoparticles displayed higher IRK activity than the mice injected with control particles, and a two-tailed t-test revealed that the difference was statistically significant (P2D-nanoparticles, 3.58±0.86 (s.e.m.) vs. control, 1.27±0.33; p<0.05). It is therefore likely that the increased glucose uptake seen in mice injected with the P2D nanoparticles (FIG. 3) is a consequence of increased IRK activity.

P2 Activation of Akt

Figures 5A, 5B, 5C:
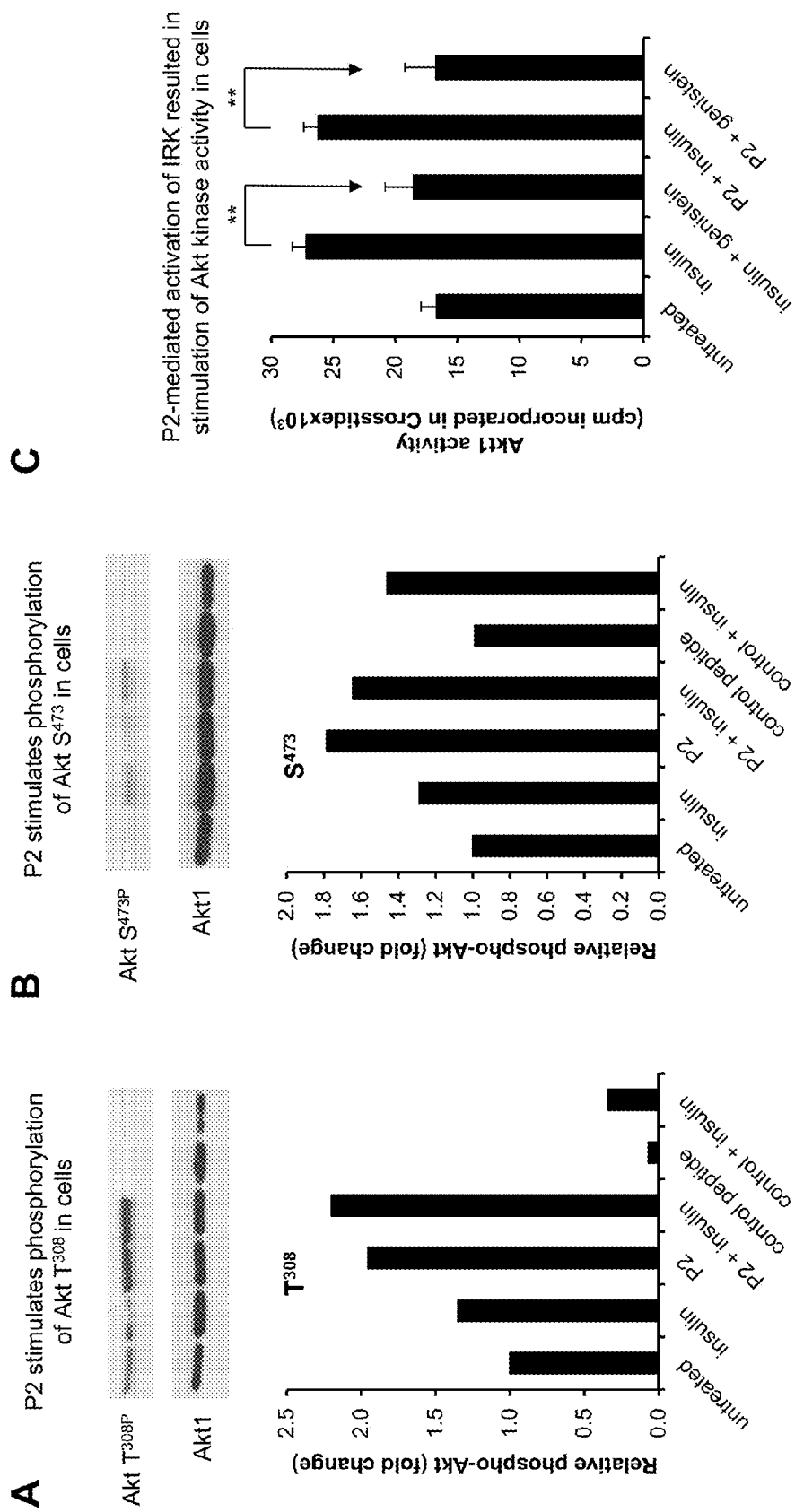
FIG. 5A depicts P2 stimulates phosphorylation of Akt T308 in cells. HEK cells were serum-starved overnight and treated with the indicated myristoylated peptides (40 µM) for 15 minutes; insulin (100 nM) was added for the final 10 minutes of treatment. Cell lysates were analyzed by Western blot, the blot was probed with antibody to phospho-Akt T308, followed by anti-Akt1 to control for loading. Signals were quantified by densitometry, and the phospho-Akt: total Akt1 ratio is expressed relative to that of untreated cells (control peptide; KKEVVGKD (SEQ ID NO: 8)).
FIG. 5B depicts P2 stimulates phosphorylation of Akt S473 in cells. A Western blot of identical lysates to those in FIG. 5A was probed with antibody to phospho-Akt S473, followed by anti-Akt1.
FIG. 5C depicts P2-mediated activation of IRK resulted in stimulation of Akt kinase activity in cells. Cells were serum starved overnight, and treated with myristoylated peptides and insulin as in FIG. 5A. Genistein (50 µM) was added to cells 30 minutes prior to treatment with peptide or insulin. Akt1 was immunoprecipitated from the lysates and kinase activity was measured using Crosstide as substrate.

Activation of IRK leads to activation of PI3K, which in turn activates PDK1 followed by recruitment of Akt to the cell membrane. Activated PDK1 phosphorylates Akt at $T^{308}$, thereby activating the kinase, after which maximum activation is achieved by phosphorylation at $S^{473}$. The phosphorylation status of these residues was examined in cells that had been treated with myristoylated P2, insulin, or both, by Western blotting. An additional control was control peptide (KKEVVGKD (SEQ ID NO: 8)), which has only distant similarity to P2, and lacks crucial residues for activity (Gibbs et al., 2014, FASEB J 28:2478-91). The blots were analyzed by densitometry to quantify the extent of phosphorylation. Peptide treatment resulted in enhanced phosphorylation at both sites (FIG. 5A and FIG. 5B). Thus, Akt kinase activity was measured in cells loaded with either P2 or the scrambled P2 peptide, P2sc. Cell lysates were immunoprecipitated with anti-Akt antibody and immunoprecipitates were examined for phosphorylation of crosstide, an Akt specific substrate. The P2-treated cells displayed increased kinase activity compared to untreated or P2sc controls (FIG. 5C); the response to P2 was indistinguishable from that to insulin. Activation of Akt in this experiment is almost certainly a consequence of activation of IRK, since the tyrosine kinase inhibitor genistein prevented Akt activation (FIG. 5C) by either insulin or P2.

P2 Treatment of Cells Inactivates GSK3

Glucose taken up by cells is either metabolized or converted to glycogen for storage. Which pathway is chosen is dependent on the activity of glycogen synthase, which is inversely regulated by its phosphorylation. Namely, both GSK3α phosphorylated at $S^{21}$ or GSK3β phosphorylated at $S^9$ by Akt are inactive, resulting in activation of glycogen synthase and hence increased glycogen synthesis. Therefore the phosphorylation status of each isoform was examined in cells treated with peptides or insulin, using the same regimen as that described for Akt phosphorylation. As expected, both GSK3 isoforms displayed enhanced phosphorylation in response to insulin or to myr-P2 (FIG. 6), as indicated by Western blotting and densitometry. Thus the consequences of activation of IRK or IGFRK by P2 manifest themselves throughout the IRK signaling pathway, and closely resemble the effects of insulin or IGF-1.

Mechanism of Action of P2 and P2D

The data presented herein describes a novel method of delivering an hBVR-based peptide to intact animals and its efficacy in ameliorating hyperglycemia in vivo. In previous studies, N-myristoylated peptides was for this purpose; these were readily taken up by cultured cells, and were shown to activate or inhibit target kinases in the same manner as was observed in vitro (Lerner-Marmarosh et al., 2007, FASEB J 21:3949-62; Lerner-Marmarosh et al., 2008, PNAS 105: 6870-5; Gibbs et al., 2014, FASEB J 28:2478-91; Miralem et al., 2012, J Biol Chem 287:24698-712). In particular, the peptide P2 (KYCCSRK (SEQ ID NO: 2)) was shown to stimulate glucose uptake by cultured cells (Gibbs et al., 2014, FASEB J 28:2478-91). Despite the successful use of the myristoylated peptides, they are likely not stable in the cell, and that they were unlikely to be of use in vivo, due to their small size, which makes them susceptible to rapid excretion via the kidney. Recently, we described a DNA-based method of peptide delivery to cells; a plasmid that expressed a fusion protein with the peptide sequence immediately following a spontaneously cleaved linker (Gibbs et al., 2014, FASEB J 28:2478-91; Hoist et al., 2006, Nat Methods 3:191-7; Provost et al., 2007, Genesis 45:625-9). The expression plasmid was delivered to cell by transfection, and increased uptake of glucose by the transfected cells was shown to persist for up to 48 hours. The stability of the peptide is unlikely to have been improved by this approach; however, continuous synthesis driven by a highly active promoter shifts the stability issue back to the retention of plasmid by the cells. Moreover, it is difficult to quantify the level of peptide in the cell at steady state, so that controlling the dose of peptide is problematic. The system described here overcomes these problems. Using a peptide with blocked N- and C-termini, as well as D-amino acids, overcomes the difficulties with peptide stability. Cultured cells treated with P2D-nanoparticles for 1 hour demonstrated a 125% increase in glucose uptake, and a 90% increase after 6 hours (FIG. 2B). In contrast, cells treated with myristoylated peptide showed no significant change in glucose after 6 hours. This increased glucose uptake in the presence of nanoparticles was dose dependent and to a large extent independent of the cell type used.

Previously, the efficacy of P2 in activating IRK was demonstrated, and it was noted the $K^1$, $K^7$ and $C^3$ were each necessary for the peptide to activate the kinase, while replacement of $C^4$ resulted in less than full activity (Gibbs et al., 2014, FASEB J 28:2478-91). Similarly, replacement of $Y^2$ with F led to reduced activation of IRK (FIG. 4C). Other peptides that included the IRK phosphorylation targets $Y^{198}$ and $Y^{228}$ were phosphorylated by IRK in vitro; neither peptide stimulated glucose uptake, and in one case, the peptide bound avidly to the active site and effectively inhibited kinase activity (Gibbs et al., 2014, FASEB J 28:2478-91). Other BVR-based peptides were also examined in this study. While none of those tested affected auto-phosphorylation of IRK, they were, to varying degrees, inhibitors of in vitro phosphorylation of insulin receptor substrate peptide. In the case of the peptide P1, this was also true in cultured cells treated with insulin or IGF-1.

Figures 6A, 6B:
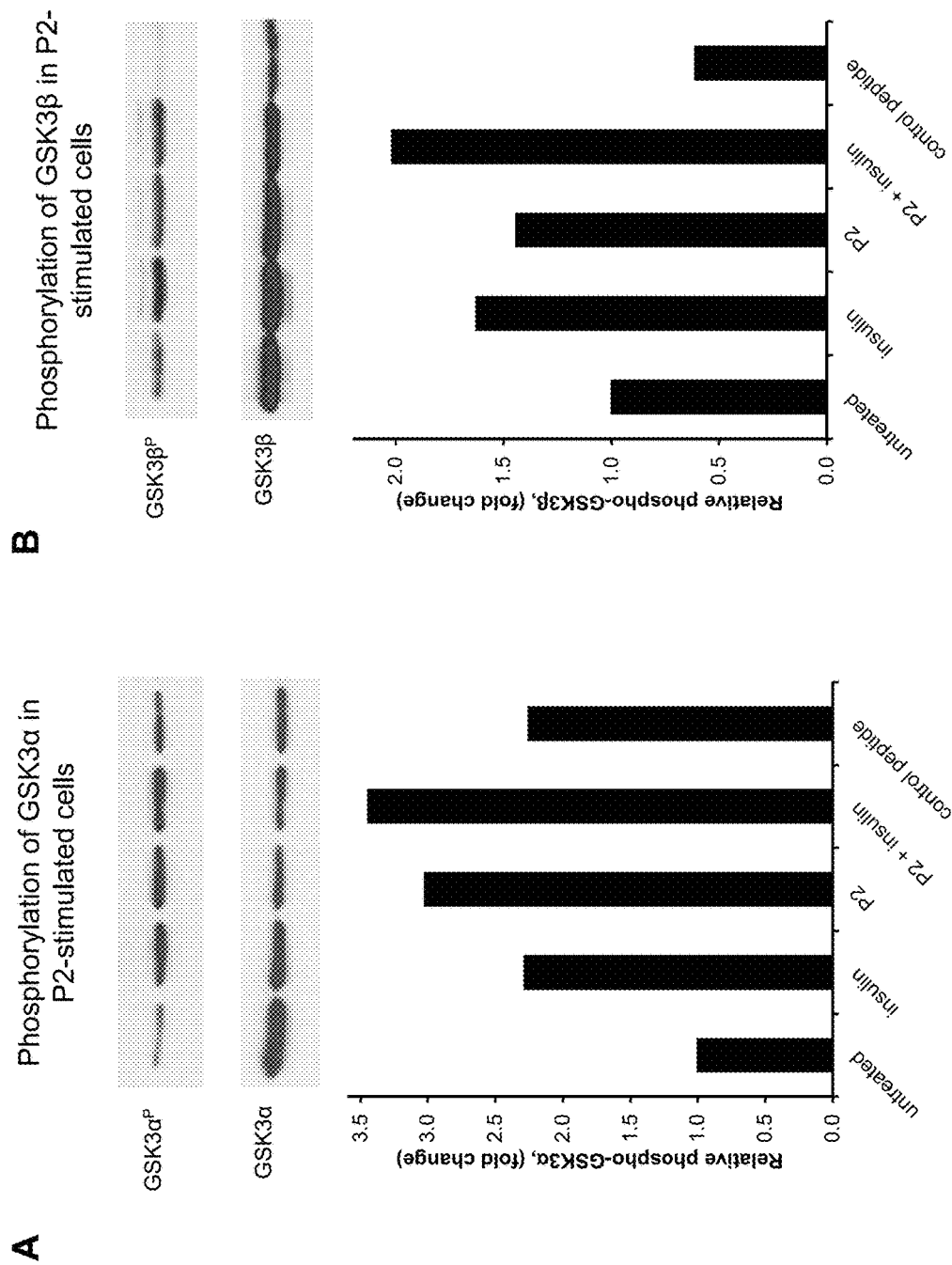
FIG. 6B depicts results of experiments demonstrating P2 inactivates GSK3.
FIG. 6A depicts Phosphorylation of GSK3α in P2-stimulated cells. Lysates of cells treated as in FIG. 5A were analyzed by Western blot; the blot was probed sequentially with antibodies to phospho-GSK3α-S21 and GSK3α. The signals were quantified by densitometry.
Figure 7:
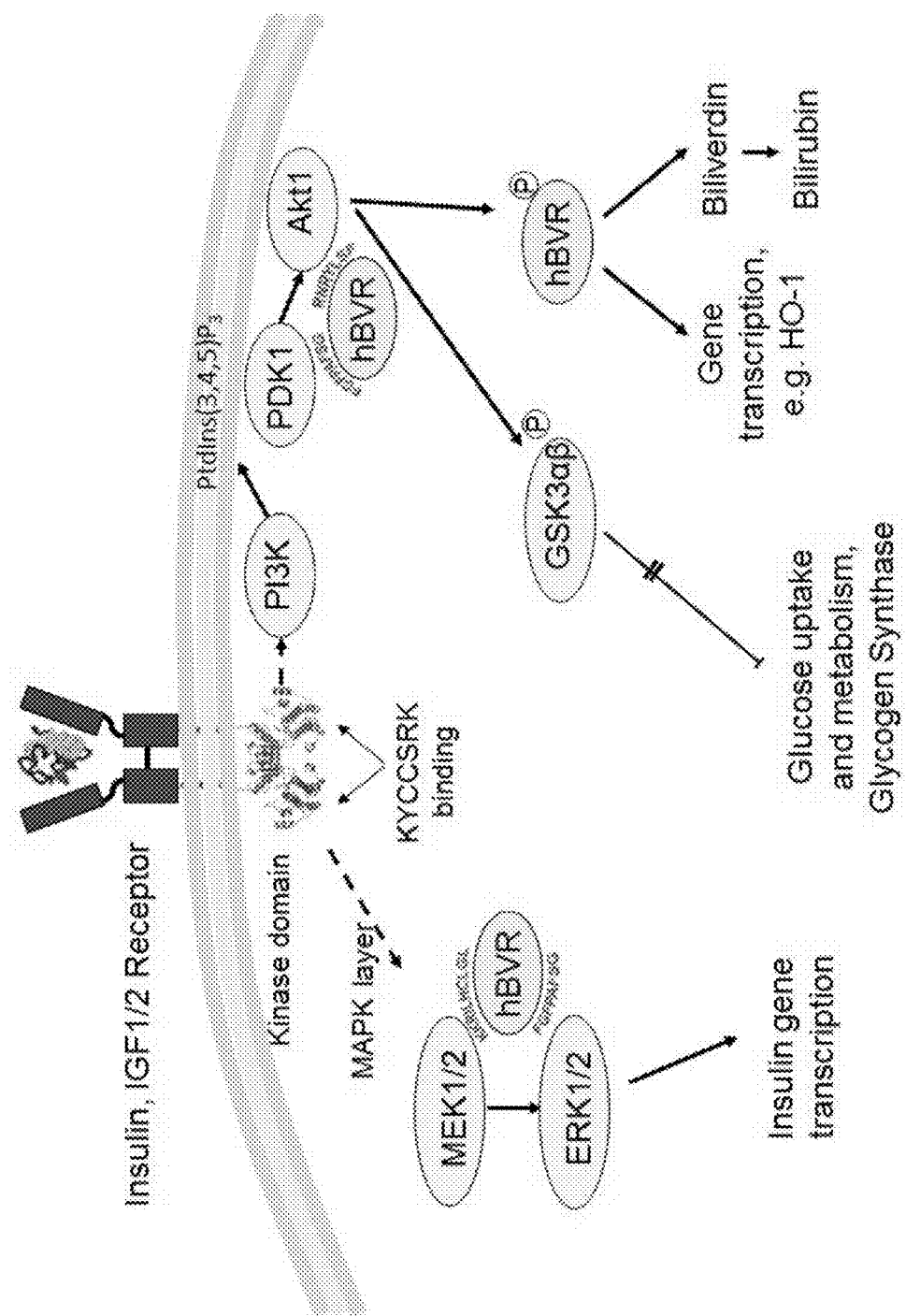
FIG. 7 depicts a schematic of P2-dependent activation of the IRK/PI3K/Akt pathway. On one side activated PI3K generates PtdIns(3,4,5)P$_3$, which interacts with the PH domain of Akt and recruits the inactive protein to the membrane, where it is phosphorylated at T$^{308}$ by the 3-phosphoinositide-dependent kinase, PDK1. On the other, BVR interacts with MEK1/2 and ERK1/2 to enhance activation of ERKs. Activation of ERK1/2 results in activation of transcription factors to stimulate expression of the insulin gene. The peptide, P2 (KYCCSRK (SEQ ID NO: 2)), binds to the receptor kinase domain, which results in activation of the multistep process leading to activation of MEK1/2 in the MAPK pathway. Specific sequence motifs in hBVR mediate its interactions with proteins in the signaling pathways, where it acts as a scaffold to bring kinases in contact with their substrates. Akts phosphorylate GSK3α,β resulting in its inactivation; the inactive GSK3s in turn cannot phosphorylate and inactivate glycogen synthase, resulting in an activation of glucose uptake.

In previous studies with both the intact hBVR protein and P2, two narrow aspects of the insulin receptor response were examined—activity of the receptor kinase, which is clearly at the start of signaling, and glucose uptake, which is the end result of activation of one of the many pathways that respond to activated IRK (Lerner-Marmarosh et al., 2005, PNAS 102:7109-14; Gibbs et al., 2014, FASEB J 28:2478-91). In this study the effect of P2 on two intermediate steps in the insulin response was examined, as summarized in FIG. 7. An early step in the insulin response pathway is activation of PI3K, which in turn results in activation of PDK1 and recruitment of Akt to the membrane. PDK1 phosphorylates $T^{308}$ in the Akt activation loop. The partially activated kinase is further phosphorylated at $S^{473}$ by several different kinases. $T^{450}$ is also phosphorylated, but this has little or no effect on the kinase activity. It is noted in FIGS. 5A and 5B that phosphorylation of both of these sites is increased in response to P2. As expected, this results in an increased activity of the kinase (FIG. 5C). The activation of Akt is also reflected in the phosphorylation of the GSK3-α and -β isozymes (FIG. 6). These proteins are inactivated by phosphorylation, leading to increased activity of their downstream targets, notably glycogen synthase (Ali et al., 2001, Chem Rev 101:2527-40; Rayasam et al., 2009, Br J Pharmacol 156:885-98), which is a key regulatory step in glycogen synthesis and glycolysis. GSK3 is also a regulator of transcription factors, including NRF2 and the AP1 subunits cFos and cJun (FIG. 7) (Salazar et al., 2006, J Biol Chem 281:14841-51; Shinohara et al., 2010, J Biol Chem 285: 8244-55; Khan et al., 2015, Neuroscience 287:66-77).

Complications of type 2-diabetes are related to oxidative stress as obesity and insulin resistance have predominant role in it (Khan and Chakrabarti, 2007, Exp Diabetes Res 2007:31867; D'Archivio et al., 2012, Eur J Clin Invest 42:70-8). In addition to its direct interaction with the kinase domain of the insulin receptor, KYCCSRK (SEQ ID NO: 2) indirectly mitigates untoward effects of hyperglycemia by regulating cellular levels of the heme oxygenase isozymes, HO-1 and HO-2 (Maines et al., 1986, J Biol Chem 261:411-9). Peptide treatment of cells stabilizes BVR mRNA and in turn, hBVR activation stabilizes HO-2 mRNA and protein (Ding et al., 2011, FASEB J 25:301-13). HO-2 is a redox-sensitive K+/Ca2+ channel-associated protein (Williams et al., 2004, Science 306:2093-7). BVR is also essential for transcriptional activation of HO-1 by AP1/2-regulated genes, cjun and CREB/ATF-2 (Kravets et al., 2004, J Biol Chem 279:19916-23; Ahmad et al., 2002, J Biol Chem 277:9226-32; Miralem et al., 2005, J Biol chem 280:17084-92). Both HO isozymes are the sole source of CO and bilirubin, which are essential components of the cellular defense mechanisms. The heme oxidation products protect against inflammation, xenograft rejection, vasoconstriction and oxidative stress (Stocker et al., 2004, Antioxid Redox Signal 6:841-9; Abraham and Kappas, 2008, Pharmacol Rev 60:79-127; Agarwal and Bolisetty, 2013, Trans Am Clin Climatol Assoc 124:111-22; Biswas et al., 2014, J Biol Chem 289:26882-94; Durante, 2011, Front iosci 16:2372-88; Naidu et al., 2008, J Immunol 181:4113-23; Nakao et al., 2005, Am J Transplant 5:282-91; Paine et al., 2010, Biochem Pharmacol 80:1895-903; Ryter et al., 2006, Physiol Rev 86:583-650; Soares and Bach, 2009, Trends Mol Med 15:50-8). Expression of HO-1 improves glucose metabolism (Hu et al., 2007, Diabetes 56:1240-7). HO-2 deficiency in HO-2(−/−) has been reported to contribute to diabetes-mediated increase in superoxide anion and renal dysfunction (Goodman et al., 2006, J Am Soc Nephrol 17:1073-81). KYCCSRK (SEQ ID NO: 2) also stimulates BVR reductase activity that is essential for conversion of biliverdin, the immediate product of HO-1 and HO-2 activity, to bilirubin (Lerner-Marmarosh et al., 2007, FASEB J 21:3949-62).

P2D delivered in nanoparticles was shown to be effective in reducing blood glucose in intact animals, when compared with a control peptide with the same amino acid composition but entirely different sequence. Circulating glucose in wt mice that had been pretreated with peptide, and then injected with glucose was decreased compared to controls in this glucose tolerance test (FIG. 3A). Similarly, genetically obese mice also showed decreased blood glucose in response to P2D treatment, and were able to better tolerate the hyperglycemicia that arose from ketamine-xylazine anesthesia (FIG. 3B and FIG. 3C. Further, treatment with P2D nanoparticles prevented glucose stimulation of insulin secretion, indicating that peptide-dependent stimulation of glucose uptake and hence lowering of circulating glucose was bypassing the physiological need for insulin.

P2D to Treat Type-1 and Type-2 Diabetes

The data obtained in this study point to a new method for controlling hyperglycemia that should be efficacious in both type-1 and type-2 diabetes. By targeting the insulin receptor kinase directly, and thereby activating the full range of downstream pathways radiating from the insulin receptor, the peptide may prove to be an alternative or addition to other drugs currently used for reducing hyperglycemia. The interaction of the peptide with IRK was examined and it was demonstrated that the peptide induces a conformational change in the kinase domain of the receptor (Gibbs et al., 2014, FASEB J 28:2478-91) as does insulin. This analysis enabled determination of peptide's binding site to the kinase domain and the conformation of the protein.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated peptide comprising an amino acid sequence of KRSCCYK (SEQ ID NO: 1), wherein each amino acid of the peptide is in D configuration (D-amino acid).

2. The peptide of claim 1, wherein the peptide further comprises an acetyl group on the N-terminus of the peptide.

3. The peptide of claim 1, wherein the peptide further comprises an amido group on the C-terminus of the peptide.

4. A composition comprising the peptide of claim 1, or a pharmaceutically acceptable carrier.

5. The composition of claim 4 is in a form of a nanoparticle.

6. The composition of claim 5, wherein the nanoparticle comprises a core comprising heparin, protamine, and the peptide.

7. The composition of claim 6, wherein the weight ratio of protamine to heparin is about 0.3:1 to about 0.6:1.

8. The composition of claim 5, wherein the nanoparticle comprises a membrane comprising cholesterol and DOTAP.

9. A method for treating diabetes in a subject, the method comprising administering to a subject an effective amount of a peptide of claim 1.

10. The method of claim 9, wherein the peptide comprises an acetyl group on the N-terminus of the peptide.

11. The method of claim 9, wherein the peptide further comprises an amido group on the C-terminus of the peptide.

12. The method of claim 9 further comprising administering a second therapeutic agent.

13. The method of claim 12, wherein the second therapeutic agent is an anti-diabetic agent.

14. The method of claim 12, wherein the second therapeutic agent is insulin.

* * * * *